(12) United States Patent  (10) Patent No.: US 8,513,444 B2
Habenschuss et al.  (45) Date of Patent: Aug. 20, 2013

(54) EPOXIDATION REACTIONS AND OPERATING CONDITIONS THEREOF

(75) Inventors: Michael Habenschuss, South Charleston, WV (US); Hwaili Soo, Charleston, WV (US); Paul V. Hinman, Charleston, WV (US); Albert C. Liu, Charleston, WV (US)

(73) Assignee: Dow Technology Investments LLC

( * ) Notice: Subject to any disclaimer, the term of this patent is extended or adjusted under 35 U.S.C. 154(b) by 379 days.

(21) Appl. No.: 12/763,477

(22) Filed: Apr. 20, 2010

(65) Prior Publication Data

US 2010/0267975 A1    Oct. 21, 2010

Related U.S. Application Data

(60) Provisional application No. 61/171,104, filed on Apr. 21, 2009.

(51) Int. Cl.
*C07D 301/10* (2006.01)
*C07D 301/03* (2006.01)

(52) U.S. Cl.
USPC .......................................... 549/536; 549/534

(58) Field of Classification Search
USPC .................................. 549/534, 536
See application file for complete search history.

(56) References Cited

U.S. PATENT DOCUMENTS

| | | | |
|---|---|---|---|
| 4,379,134 A | 4/1983 | Weber et al. | |
| 4,759,313 A | 7/1988 | Dye | |
| 4,761,394 A | 8/1988 | Lauritzen | |
| 4,766,105 A | 8/1988 | Lauritzen | |
| 4,769,047 A | 9/1988 | Dye | |
| 4,806,518 A | 2/1989 | Boxhoorn et al. | |
| 4,808,738 A | 2/1989 | Lauritzen | |
| 4,820,675 A | 4/1989 | Lauritzen | |
| 4,829,044 A | 5/1989 | Boxhoorn | |
| 4,831,162 A | 5/1989 | Nakajima | |
| 4,833,261 A | 5/1989 | Lauritzen | |
| 4,874,739 A | 10/1989 | Boxhoorn | |
| 4,874,879 A | 10/1989 | Lauritzen | |
| 4,908,343 A | 3/1990 | Bhasin | |
| 4,916,243 A | 4/1990 | Bhasin et al. | |
| 5,011,807 A | 4/1991 | Hayden et al. | |

(Continued)

FOREIGN PATENT DOCUMENTS

| | | |
|---|---|---|
| CA | 1286687 | 7/1991 |
| EP | 352850 | 1/1990 |
| EP | 0480537 | 4/1992 |
| GB | 1314613 | 4/1973 |

OTHER PUBLICATIONS

Kirk-Othmer's Encyclopedia of Chemical Technology, 4th ed., vol. 9, 1994, pp. 915-959.

(Continued)

*Primary Examiner* — Taylor Victor Oh

(57) ABSTRACT

A method of producing an alkylene oxide includes passing a reaction mixture comprising alkylene, oxygen and a gaseous chlorine-containing promoter species over a supported catalyst containing silver and a promoting amount of rhenium to undergo an epoxidation reaction at a first operating condition. The method further includes subsequently performing the epoxidation reaction at a preferred operating condition. The preferred operating condition is characterized by an efficiency of the epoxidation reaction toward the alkylene oxide where the efficiency is lower than that of a maximum efficiency achievable at an operating temperature corresponding to the preferred operating condition.

10 Claims, 8 Drawing Sheets

(56) References Cited

U.S. PATENT DOCUMENTS

| | | |
|---|---|---|
| 5,059,481 A | 10/1991 | Lustig et al. |
| 5,063,195 A | 11/1991 | Jin et al. |
| 5,102,848 A * | 4/1992 | Soo et al. .................... 502/218 |
| 5,143,877 A | 9/1992 | Geus |
| 5,145,824 A | 9/1992 | Buffum |
| 5,155,242 A | 10/1992 | Shankar |
| 5,187,140 A | 2/1993 | Thorsteinson et al. |
| 5,228,484 A | 7/1993 | Johnson |
| 5,262,551 A | 11/1993 | Horrell et al. |
| 5,364,826 A | 11/1994 | Kemp |
| 5,380,697 A | 1/1995 | Matusz |
| 5,380,885 A | 1/1995 | Kemp |
| 5,384,302 A | 1/1995 | Gerdes et al. |
| 5,387,751 A | 2/1995 | Hayden et al. |
| 5,418,202 A | 5/1995 | Evans |
| 5,447,897 A | 9/1995 | Kemp |
| 5,486,628 A | 1/1996 | Kemp |
| 5,504,053 A | 4/1996 | Chou et al. |
| 5,519,152 A | 5/1996 | Gorcester |
| 5,545,603 A | 8/1996 | Kemp |
| 5,597,773 A | 1/1997 | Evans |
| 5,663,385 A | 9/1997 | Kemp |
| 5,703,253 A | 12/1997 | Evans |
| 5,719,299 A | 2/1998 | Raa |
| 5,739,075 A | 4/1998 | Matusz |
| 5,770,746 A | 6/1998 | Cooker et al. |
| 5,801,259 A | 9/1998 | Koweleski |
| 5,840,932 A | 11/1998 | Evans |
| 5,874,653 A | 2/1999 | Van Kruchten |
| 5,929,259 A | 7/1999 | Lockemeyer |
| 6,080,897 A | 6/2000 | Kawabe |
| 6,511,938 B1 | 1/2003 | Liu et al. |
| 6,831,037 B2 | 12/2004 | Szymanski et al. |
| 7,615,655 B2 | 11/2009 | Zhang et al. |
| 7,657,331 B2 | 2/2010 | Chipman et al. |
| 7,803,957 B2 | 9/2010 | Rizkalla |
| 2004/0014999 A1 | 1/2004 | Chipman et al. |
| 2004/0198993 A1 | 10/2004 | Matusz |
| 2006/0009647 A1 | 1/2006 | Yeates et al. |
| 2007/0032670 A1 | 2/2007 | Zhang et al. |
| 2007/0111886 A1 | 5/2007 | Serafin et al. |
| 2009/0177000 A1 | 7/2009 | Natal et al. |

OTHER PUBLICATIONS

Berty, "Inhibitor Action of Chlorinated Hydrocarbons in the Oxidation of Ethylene to Ethylene Oxide", Chemical Engineering Communications, vol. 82 (1989), p. 229-232.

Berty, "Ethylene Oxide Synthesis", Applied Industrial Catalysis, vol. 1 (1983), p. 207-238.

Katsumi, Method for Manufacturing Olefin Oxide Using Rhenium-Containing Catalyst, Patent abstract of JP2002-148351, Mar. 9, 2002.

International Search Report and Written Opinion for PCT/US2010/031673.

International Search Report and Written Opinion for PCT/US2010/031533.

International Search Report and Written Opinion for PCT/US2010/031668.

Notice of Opposition to European Patent No. 1,458,699 B1, filed with the European Patent Office by The Dow Chemical Company, Midland, MI, USA, Aug. 3, 2006.

Notice of Opposition to European Patent No. 1,458,699 B1, filed with the European Patent Office by The Dow Chemical Company, Midland, MI, USA, Jan. 18, 2006.

Reply in Opposition to European Patent No. 1,458,699 B1, filed with the European Patent Office by The Dow Chemical Company, Midland, MI, USA, Aug. 22, 2008.

* cited by examiner

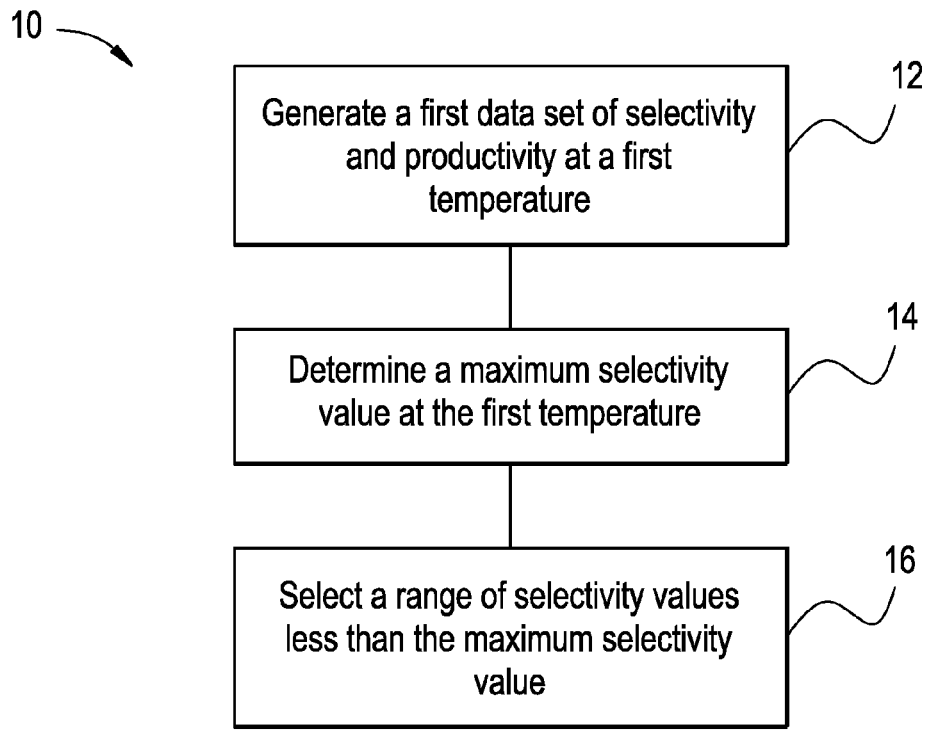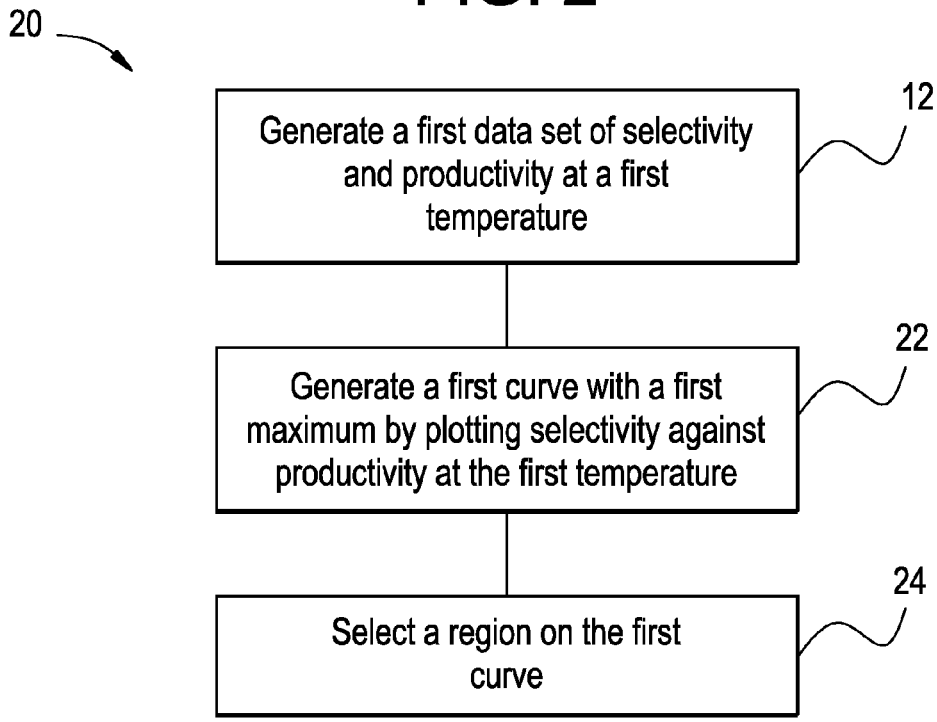

EPOXIDATION REACTIONS AND OPERATING CONDITIONS THEREOF

CROSS-REFERENCE TO RELATED APPLICATION(S)

This application claims benefit of priority from U.S. Provisional Patent Application No. 61/171,104, filed Apr. 21, 2009, which application is incorporated by reference herein in its entirety.

FIELD OF THE INVENTION

The invention relates generally to operating epoxidation reactions at a preferred operating condition. The invention also relates to methods of determining the preferred operating condition.

BACKGROUND OF THE INVENTION

Alkylene oxides are known for a multiplicity of utilities. Ethylene oxide, for example, is used to produce ethylene glycol, which is used as an automotive coolant, as antifreeze, and in preparing polyester fibers and resins, nonionic surfactants, glycol ethers, ethanolamines, and polyethylene polyether polyols. Propylene oxide is used to produce propylene glycol and polypropylene polyether polyols, which are used in polyurethane polymer applications.

The production of alkylene oxides via catalytic epoxidation of olefins in the presence of oxygen using supported silver based catalysts is known. By introducing a promoting amount of rhenium in the silver catalyst, the efficiency of the epoxidation reaction can be greatly improved. Epoxidation reactions are typically carried out in presence of gaseous reaction promoters such as chlorinated hydrocarbons which increases the efficiency of the reaction. For silver catalysts containing rhenium, in addition to increasing efficiency, increasing the amount of chlorinated hydrocarbons typically increases the activity of the epoxidation reaction. As a result the reaction can be conducted at lower temperatures while maintaining constant alkylene oxide production.

The prior art teaches that epoxidation reactions can be run at maximum efficiency at a temperature by adjusting the concentration of the chlorinated hydrocarbons. This can lead to running the reaction at a higher than necessary (or desirable) temperature, leading to increased risk of over-chlorination of the catalyst and hence deactivation of the catalyst, and also cause difficulty in maintaining a target ethylene oxide production rate due to the catalyst's strong activity dependence on chlorine level.

It is desirable to provide an improved method of producing ethylene oxide which resolves some of the issues associated with operating the epoxidation reaction at optimal efficiency.

BRIEF DESCRIPTION

The present invention allows the production of the same amount of alkylene oxide at both higher efficiency (resulting in raw material savings, and less greenhouse gas generation) and lower temperature (resulting in less by-product impurities and less Ag sintering) than earlier processes. Higher selectivity and lower operating temperatures can be achieved through the use of this invention without the need for a control system capable of automatically maintaining constant productivity or conversion. Operation at lower temperatures can enable longer catalyst lifetimes as well. The present invention allows the determination of a set of operating conditions that results in a higher efficiency, for a given productivity, than would be obtained by earlier processes.

In one embodiment, a method of producing an alkylene oxide is provided. The method includes passing a reaction mixture comprising alkylene, oxygen and a gaseous chlorine-containing promoter species over a supported catalyst containing silver and a promoting amount of rhenium to undergo an epoxidation reaction at a first operating condition to form an alkylene oxide in a reactor. The method further includes subsequently performing the epoxidation reaction within the reactor at a preferred operating condition. The preferred operating condition is characterized by an efficiency of the epoxidation reaction toward the alkylene oxide where the efficiency is lower than that of a maximum efficiency achievable at an operating temperature corresponding to the preferred operating condition.

In another embodiment, a method of determining a preferred operating condition of an epoxidation reaction over a catalyst containing silver and a promoting amount of rhenium in the presence of a gaseous chlorine-containing promoter species is provided. The method includes determining a derivative of efficiency to productivity of the epoxidation reaction as a function of overall catalyst chloriding effectiveness value at a fixed operating temperature. The preferred operating condition is characterized by the derivative which is in a range of about −1 to about −4 when the efficiency of the epoxidation reaction to form alkylene oxide is expressed in percent and productivity of the epoxidation reaction is expressed as the concentration of alkylene oxide in the reactor outlet stream, in mole percent.

In yet another embodiment, a method of determining a preferred operating condition of an epoxidation reaction in the presence of a supported catalyst containing silver and a promoting amount of rhenium in the presence of a gaseous chlorine-containing promoter species is provided. The method includes generating a first data set on efficiency and productivity of the epoxidation reaction at least three overall catalyst chloriding effectiveness values at a first temperature. The method further includes determining a maximum efficiency value at the first temperature from the first data set. The method further includes selecting a range of efficiency values lower than the maximum efficiency value. The range of efficiency values corresponds to higher productivity of the epoxidation reaction than that achievable when the epoxidation reaction is operated at maximum efficiency and at the first temperature. The range of efficiency values corresponds to the preferred operating condition.

DRAWINGS

These and other features, aspects, and advantages of the present invention will become better understood when the following detailed description is read with reference to the accompanying drawings in which like characters represent like parts throughout the drawings, wherein:

FIG. 1 is a flowchart of a method of determining a preferred operating condition according to embodiments of the present invention;

FIG. 2 is a flowchart of another method of determining a preferred operating condition according to one embodiment of the present invention;

DETAILED DESCRIPTION

Figure 3:
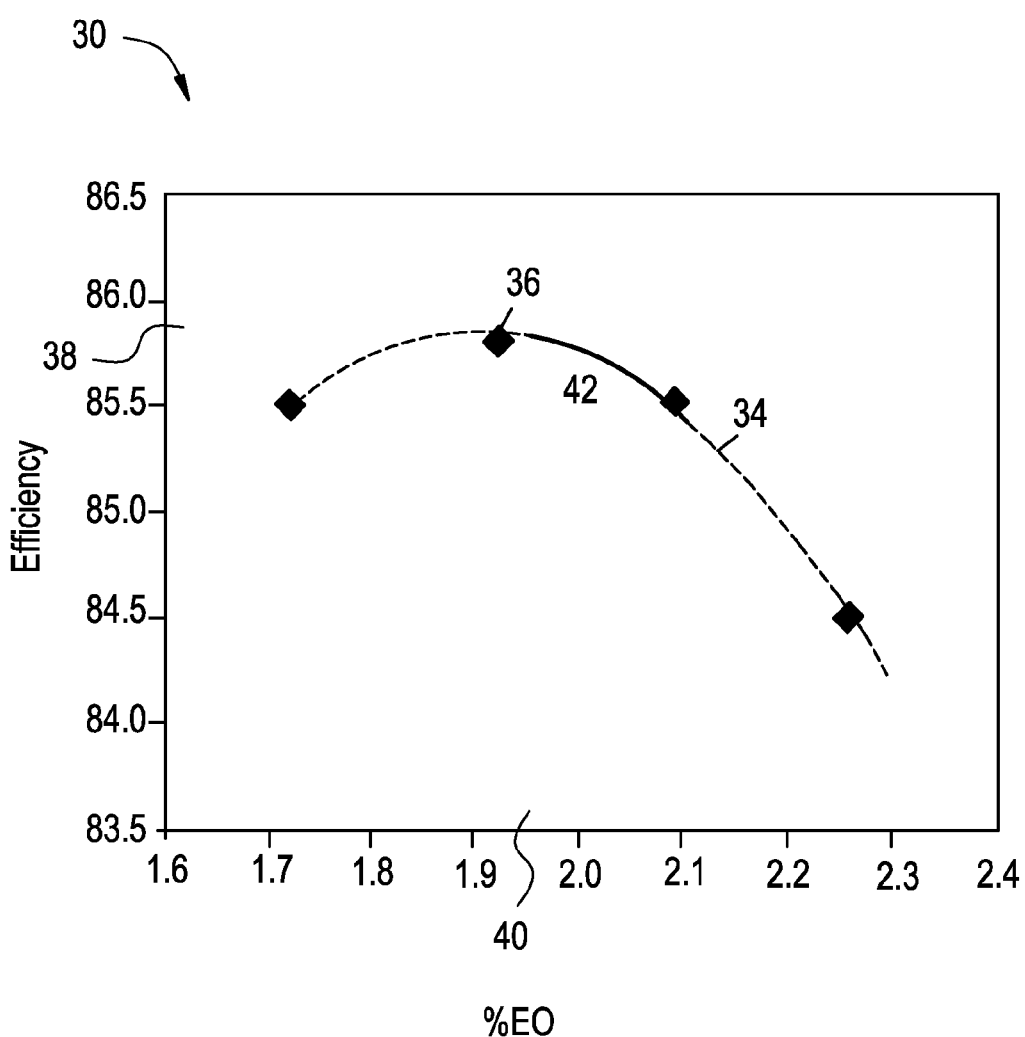
FIG. 3 is an illustration of a plot of efficiency against productivity of an epoxidation reaction obtained using the method shown in FIG. 2, in accordance with embodiments of the present invention.

In a typical epoxidation reaction, an alkylene, such as ethylene, reacts with oxygen or an oxygen-containing gas in presence of a supported silver catalyst in a reactor to form an alkylene oxide such as ethylene oxide. The epoxidation reaction can be characterized in terms of "activity", "productivity", "yield" and/or "selectivity" of the epoxidation reaction.

The activity of the epoxidation reaction can be quantified in a number of ways, one being the mole percent of alkylene oxide contained in an outlet stream of the reactor relative to that in the inlet stream (the mole percent of alkylene oxide in the inlet stream typically, but not necessarily, approaches zero percent) while the reactor temperature is maintained substantially constant; and another being the temperature required to maintain a given rate of alkylene oxide production. In many instances, activity is measured over a period of time in terms of the mole percent of alkylene oxide produced at a specified constant temperature. The activity can be defined as the reaction rate towards the alkylene oxide formation per unit of catalyst volume in the reactor. Alternatively, activity can be measured as a function of the temperature required to sustain production of a specified constant mole percent of alkylene oxide, such as ethylene oxide, given other conditions such as pressure and total moles in the feed.

The productivity of the reaction is a measure of the reaction rate normalized by the amount of catalyst. In many instances, productivity can be expressed as moles or kilograms of alkylene oxide produced per hour per volume of the catalyst measured as the packed volume of the reactor. In certain instances, the productivity can be expressed as mole percent of alkylene oxide in the outlet stream of the reactor at specified process conditions such as a space velocity.

The "selectivity" of the epoxidation reaction, which is synonymous with "efficiency," refers to the relative amount (as a fraction or in percent) of converted or reacted olefin that forms a particular product. For example, the "efficiency to alkylene oxide" refers to the percentage on a molar basis of converted or reacted alkylene that forms alkylene oxide.

"Deactivation", as used herein, refers to a permanent loss of activity and/or efficiency that is a decrease in activity and/or efficiency that cannot be recovered. Lower rates of deactivation are generally desirable.

The "yield" of alkylene oxide refers to the net number of moles of alkylene oxide produced by the process divided by the net number of moles of olefin fed to the process for any given time period.

The term "first operating condition" as used herein, refers to an operating condition at any given time of the epoxidation reaction and is applicable throughout the life of the catalyst. With respect to operation of the epoxidation reaction, the term "operating condition", as used herein, is defined (or expressed) in terms of the following components: temperature; and pressure; and gas hourly space velocity; and composition and/or concentrations of the reaction mixture. In some embodiments, the first operating condition can be at the beginning of catalyst life, while in certain other embodiments, the first operating condition can be a period later in the life of the catalyst. Embodiments of the present invention provide methods for determining the preferred operating condition and also methods to perform the epoxidation reaction at the preferred operating condition subsequent to a first operating condition. In some embodiments, the method can include a single first operating condition prior to achieving the preferred operating condition. In certain other embodiments, the method can include a number of first operating conditions prior to achieving the preferred operating condition.

The inventors surprisingly have found that instead of operating at maximum efficiency at a given temperature, the epoxidation reaction is operated at a "preferred operating condition". As defined herein, the term "preferred operating condition" corresponds to a desired combination of productivity and efficiency of the epoxidation reaction and which can be achieved from a first operating condition.

In one embodiment, the preferred operating condition is characterized by a desired productivity at which the efficiency of the epoxidation reaction is maximized. In yet another embodiment, the methods of the present invention can provide a preferred operating condition that corresponds to a temperature of operation that is lower than the temperature of operation using the method of optimal efficiency taught by the prior art. Advantageously, the preferred operating condition as set forth in the present application is applicable at any period during life of the catalyst. The preferred operating condition, according to one embodiment of the present invention, corresponds to an efficiency of the epoxidation reaction which is lower than that of a maximum efficiency at the same operating temperature, as well as a productivity which is higher than a productivity associated with performing the epoxidation reaction at maximum efficiency and at the same operating temperature. Embodiments of the present invention also provide methods of determining the preferred operating condition.

In one embodiment, a method of producing an alkylene oxide is provided. The method includes passing a reaction mixture comprising alkylene, oxygen and a gaseous chlorine-containing promoter species over a supported catalyst comprising silver and a promoting amount of rhenium to undergo an epoxidation reaction at a first operating condition to form an alkylene oxide in a reactor. The epoxidation reaction is subsequently performed at the preferred operating condition.

Determining operating conditions under which epoxidation reactions can be performed at a maximum efficiency can be accomplished by varying the "overall catalyst chloriding effectiveness" (as defined later herein) value at an operating temperature while keeping other components of an operating condition substantially unchanged. For example, the overall catalyst chloriding effectiveness value may be varied by changing the concentration of one or more gaseous chlorine-containing promoter species and/or the concentration of one or more non-chlorine containing hydrocarbon species. It is preferred that the concentration of alkylene is not varied. It is most preferred to vary the overall catalyst chloriding effectiveness by changing the concentration of a gaseous chlorine-containing promoter species, for example, by changing its feed rate to the reactor. At a particular overall catalyst chloriding effectiveness value, hereinafter referred to as an "overall catalyst chloriding effectiveness value at maximum efficiency", the epoxidation reaction exhibits maximum efficiency at the operating temperature, which is a maximum efficiency achievable at that operating temperature given the other components of the operating condition remain substantially unchanged.

Increasing the overall catalyst chloriding effectiveness value from the overall catalyst chloriding effectiveness value at maximum efficiency causes a decrease of the efficiency of the epoxidation reaction towards alkylene oxide formation.

As compared to the first operating condition, the preferred operating condition is operated at an operating temperature and an overall catalyst chloriding effectiveness value, where at least one of the operating temperature and the overall catalyst chloriding effectiveness value is different from those of the first operating condition.

In one embodiment, performing the epoxidation reaction at the preferred operating condition comprises operating the reactor at a substantially fixed temperature. In one embodiment, the preferred operating condition is further characterized by an overall catalyst chloriding effectiveness value and the maximum efficiency achievable at an operating temperature corresponding to the preferred operating condition is the maximum efficiency achievable under the same reaction conditions as the preferred operating condition except that the overall catalyst chloriding effectiveness value is lower. In one embodiment, only the overall catalyst chloriding effectiveness value should be different between the preferred operating condition and those yielding the maximum efficiency.

Alkylenes employed in embodiments of the present invention are characterized by the following formula (I):

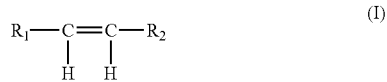

(I)

where $R_1$ and $R_2$ are each individually selected from hydrogen and lower monovalent radicals, preferably $C_1$-$C_6$ alkyl radicals including methyl, ethyl, propyl, butyl and higher homologues having up to six carbon atoms. In some embodiments, $R_1$ and $R_2$ are each individually selected from hydrogen, methyl, ethyl and propyl. In one embodiment, both of $R_1$ and $R_2$ are hydrogen and the preferred alkylene is ethylene. In some embodiments, the alkylene is propylene, where $R_1$ is hydrogen and $R_2$ is methyl. The corresponding alkylene oxides or epoxides produced are preferably characterized by the following structural formula (II):

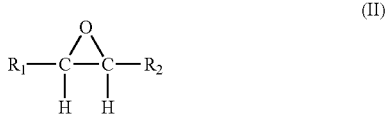

(II)

where $R_1$ and $R_2$ are identified herein in connection with the reactant alkylene. In some embodiments, the alkylene oxide is ethylene oxide (i.e., $R_1$ and $R_2$ are both hydrogen). In certain embodiments, the alkylene oxide is propylene oxide (i.e., $R_1$ is hydrogen and $R_2$ is methyl). Other exemplary alkylene oxides include oxides with the formula (II), where $R_1$ and $R_2$ are each individually selected from hydrogen and lower monovalent radicals, preferably $C_1$-$C_6$ alkyl radicals.

Suitable reactors for the epoxidation reaction include fixed bed reactors, fixed bed tubular reactors, continuous stirred tank reactors (CSTR), fluid bed reactors and a wide variety of reactors that are well known to those skilled in the art. The desirability of recycling unreacted feed, or employing a single-pass system, or using successive reactions to increase alkylene conversion by employing reactors in series arrangement can also be readily determined by those skilled in the art. The reaction pressure varies depending on the design of the reactor, but is typically in the range of about 1000 kPa (kilopascal) to about 2500 kPa absolute. In some embodiments, the pressure of the reactor is in a range of about 1800 kPa to about 2500 kPa absolute. The temperature of the reactor is an important operating parameter. The epoxidation reaction is carried out at a temperature that is preferably at least about 200° C., more preferably at least about 210° C., and most preferably at least about 220° C. Reactor temperatures of no more than about 300° C. are preferred, more preferably not more than about 290° C., and most preferably not more than about 280° C. The temperature of the reaction can be measured at various points within the reactor, such as, but not limited to, temperature at the catalyst bed or temperature of the gases comprising the outlet stream from the reactor. In certain embodiments, a coolant temperature such as an inlet coolant temperature corresponding to the coolant temperature at the point where the coolant is provided to the coolant side of the reactor can be used. The particular mode of operation, for example, conditions such as temperature and/or pressure, selected is usually dictated by process economics.

The epoxidation reaction can be air-based or oxygen-based, see Kirk-Othmer's Encyclopedia of Chemical Technology, 3rd ed., Vol. 9, 1980, p. 445-447. The oxygen can be provided to the process as pure molecular oxygen, or alternatively, as an oxygen-containing gas, wherein the gas may further contain one or more gaseous components, for example, gaseous diluents, such as nitrogen, helium, methane, and argon, which are essentially inert with respect to the oxidation process. Suitable oxygen-containing gas includes air. Additionally, the oxygen-containing gas can contain one or more of the following gaseous components including water, carbon dioxide, and various gaseous promoters or their by-products. The oxygen concentration in the reaction mixture may vary over a wide range. In practice, flammability of the reaction mixture is a major consideration which can limit the oxygen concentration. In some embodiments, the oxygen concentration is at least about 1 mole percent, and more preferably at least about 2 mole percent. In certain embodiments, the oxygen concentration is no greater than about 15 mole percent, and more preferably no greater than about 12 mole percent of the reaction mixture.

The alkylene concentration in the reaction mixture can vary over a wide range. In some embodiments, the alkylene concentration is at least about 18 mole percent, and more preferably at least about 20 mole percent. In certain embodiments, the concentration of alkylene in the reaction mixture is no greater than about 50 mole percent, and more preferably no greater than about 40 mole percent. The reaction mixture may further contain other hydrocarbons, such as ethane.

The relative volumetric ratio of alkylene to oxygen in the reaction mixture can range in accordance with any of such known conventional values. Typically, the volumetric ratio of alkylene to oxygen in the reaction mixture can vary from about 1/1 to about 10/1. Likewise, the quantity of inert gases, diluents, or other gaseous components, such as water, carbon dioxide, gaseous promoters and gaseous by-product inhibitors, can vary in accordance with known conventional ranges as found in the art.

In some embodiments, the catalyst is a supported catalyst. Suitable support materials of the catalyst can include porous refractory carrier or materials that are relatively inert in the presence of the reaction mixture introduced for epoxidation and the product epoxide, and are able to withstand preparation conditions when converted into catalyst. For example, support can be composed of alpha-alumina, silicon carbide, silicon dioxide, zirconia, magnesia, pumice, zeolites, charcoal, various clays, alkaline earth metal carbonates, such as calcium carbonate and mixtures thereof. In one embodiment, the support is composed of alpha-alumina.

There are many well-known methods of preparing supports suitable for use in alkylene oxide catalysts. Some of such methods are described in, for example, U.S. Pat. Nos. 4,379,134; 4,806,518; 5,063,195; 5,384,302; 6,831,037 and the like. For example, an alpha-alumina support of at least 95% purity can be prepared by compounding (mixing) the raw materials, extrusion, drying and a high temperature calcination. In this case, the starting raw materials usually include one or more alpha-alumina powder(s) with different properties, a clay-type material which may be added as binder to provide physical strength, and a burnout material (usually an organic compound) used in the mix to provide desired porosity and/or pore size distribution after its removal during the calcination step. The levels of impurities in the finished support are determined by the purity of the raw materials used, and their degree of volatilization during the calcination step. Common impurities may include silica, alkali and alkaline earth metal oxides and trace amounts of metal and/or non-metal-containing additives. Another method for preparing a support having particularly suitable properties for alkylene oxide catalyst usage comprises optionally mixing zirconium silicate with boehmite alumina (AlOOH) and/or gamma-alumina, peptizing the aluminas with a mixture containing an acidic component and halide anions (preferably fluoride anions) to provide peptized halogenated alumina, forming (for example, by extruding or pressing) the peptized halogenated alumina to provide formed peptized halogenated alumina, drying the formed peptized halogenated alumina to provide dried formed alumina, and calcining the dried formed alumina to provide pills of modified alpha-alumina support.

There have been employed alumina which has a very high purity, that is, at least 98 wt. % alpha-alumina, any remaining components being silica, alkali metal oxides (for example, sodium oxide) and trace amounts of other metal-containing and/or non-metal-containing additives or impurities. Likewise, there have been employed alumina of lower purity, that is, about 80 wt. % alpha-alumina, the balance being one or more of amorphous and/or crystalline alumina and other alumina oxides, silica, silica alumina, mullite, various alkali metal oxides (for example, potassium oxide and cesium oxide), alkaline earth metal oxides, transition metal oxides (for example, iron oxide and titanium oxide), and other metal and non-metal oxides. In addition, the material used to make the support may comprise compounds which have been known for improving catalyst performance, for example, rhenium, (such as rhenates) and molybdenum.

In one embodiment, the support material comprises at least about 80 weight percent alpha-alumina and comprises less than about 30 parts per million acid-leachable alkali metals by weight, the weight percent of the alpha-alumina and the concentration of the acid-leachable alkali metals being calculated on the weight of the support, where the acid-leachable alkali metals are selected from lithium, sodium, potassium, and mixtures thereof.

The alpha-alumina support preferably has a pore volume of at least about 0.3 cm$^3$/g, and more preferably, from about 0.4 cm$^3$/g to about 2.0 cm$^3$/g; and a median pore diameter from about 1 to about 50 microns.

The alpha-alumina support preferably has a specific surface area of at least about 0.5 m$^2$/g, and more preferably, at least about 0.7 m$^2$/g. The surface area is typically less than about 10 m$^2$/g, and preferably, less than about 5 m$^2$/g.

In one embodiment, the alpha-alumina support includes particles each of which has at least one substantially flat major surface having a lamellate or platelet morphology which approximates the shape of a hexagonal plate (some particles having two or more flat surfaces), at least 50 percent of which (by number) have a major dimension of less than about 50 microns.

In one embodiment, the alpha-alumina support comprises zirconium silicate (zircon), present substantially as zirconium silicate in the finished support, more preferably, in an amount up to about 4 weight percent, calculated on the weight of the support.

The alpha-alumina support can be of any suitable shape. Exemplary shapes of the support includes pills, chunks, tablets, pieces, pellets, rings, spheres, wagon wheels, toroids having star shaped inner and/or outer surfaces, and the like. The support can be of any size suitable for employment in reactors. For example, in a fixed bed ethylene oxide reactor having a plurality of parallel elongated tubes (in a suitable shell) about 1 to 3 inches (2.5 to 7.5 cm) outer diameter and about 15 to 45 feet (4.5 to 13.5 m) long filled with catalyst, it is desirable to employ alpha alumina support having a rounded shape, such as, for example, spheres, pellets, rings, tablets, and the like, having diameters from about 0.1 inch (0.25 cm) to about 0.8 inch (2 cm).

In some embodiments, catalysts for the production of alkylene oxide, for example, ethylene oxide or propylene oxide, may be prepared with the aforementioned supports by impregnating the support with a solution of one or more silver compounds, depositing the silver throughout the pores of the support and reducing the silver compound to metallic silver, as is well known in the art. See for example, Liu, et al., U.S. Pat. No. 6,511,938 and Thorsteinson et al., U.S. Pat. No. 5,187,140, incorporated herein by reference.

Generally, the support is impregnated with a catalytic amount of silver, which is any amount of silver capable of catalyzing the direct oxidation of the alkylene with oxygen or an oxygen-containing gas to the corresponding alkylene oxide. In making such a catalyst, the support is typically impregnated (one or more times) with one or more silver compound solutions sufficient to allow the silver to be supported on the support in an amount greater than about 5 percent, greater than about 10 percent, greater than about 15 percent, greater than about 20 percent, greater than about 25 percent, greater than about 27 percent, and more preferably greater than about 30 percent by weight, based on the weight of the catalyst. Typically, the amount of silver on the support is less than about 70 percent, and more preferably, less than about 50 percent by weight, based on the weight of the catalyst.

Although silver particle size in the finished catalyst is important, the range is not narrow. A suitable silver particle size can be in the range of about 10 angstroms to about 10,000 angstroms in diameter. A preferred silver particle size ranges from greater than about 100 angstroms to less than about 5,000 angstroms in diameter. It is desirable that the silver be relatively uniformly dispersed within, throughout, and/or on the alpha-alumina support.

In some embodiments, the impregnating solution can include the rhenium promoter and/or co-promoters and any mixtures thereof. In certain other embodiments, the promoter and the co-promoter can be added before the silver impregnation, or after the silver impregnation or in different impregnations from each other. The promoters, as used herein, are materials which, when present in combination with particular catalytic materials, for example, silver, benefit one or more aspect of catalyst performance or otherwise act to promote the catalyst's ability to make a desired product, for example ethylene oxide or propylene oxide. As used herein, the term "co-promoter" refers to a material which, when combined with a promoter, increases the promoting effect of the promoter. In addition, promoters may also be referred to as "dopants". The promoter and the co-promoters in themselves are generally not considered catalytic materials. The presence of promoter and/or co-promoters in the catalyst have been shown to contribute to one or more beneficial effects on the catalyst performance, for example enhancing the rate or amount of production of desired product, reducing the temperature required to achieve a suitable rate of reaction, reducing the rates or amounts of undesired reactions, etc. Competing reactions occur simultaneously in the reactor, and a critical factor in determining the effectiveness of the overall process is the measure of control one has over these competing reactions. A material which is termed a promoter or a co-promoter of a desired reaction can be an inhibitor of another reaction, for example a combustion reaction. What is significant is that the effect of the promoter and/or the co-promoter on the overall reaction is favorable to the efficient production of the desired product, for example ethylene oxide. The concentration of the one or more promoter and/or co-promoters present in the catalyst may vary over a wide range depending on the desired effect on catalyst performance, the other components of a particular catalyst, the physical and chemical characteristics of the support, and the epoxidation reaction conditions.

There are at least two types of promoters-solid promoters and gaseous promoters. The solid and/or gaseous promoters are provided in a promoting amount. As used herein, the term "promoting amount" refers to an amount of a component of the catalysts that works effectively to provide an improvement in one or more of the catalytic properties of that catalyst when compared to a catalyst not containing said component. Examples of catalytic properties include, inter alia, operability (resistance to run-away), efficiency, activity, conversion, stability and yield. It is understood by one skilled in the art that one or more of the individual catalytic properties may be enhanced by the "promoting amount" while other catalytic properties may or may not be enhanced or may even be diminished. It is further understood that different catalytic properties may be enhanced at different operating conditions. For example, a catalyst having enhanced efficiency at one one operating condition may be operated at a different condition wherein the improvement shows up in the activity rather than the efficiency.

The promoting effect provided by the promoters can be affected by a number of variables such as for example, operating condition, catalyst preparative techniques, surface area and pore structure and surface chemical properties of the support, the silver and co-promoter content of the catalyst, the presence of other cations and anions present on the catalyst. The presence of other activators, stabilizers, promoters, enhancers or other catalyst improvers can also affect the promoting effects.

Examples of well-known solid promoters for catalysts used to produce ethylene oxide include compounds of rhenium, potassium, rubidium, cesium, sulfur, manganese, molybdenum, and tungsten. During the reaction to make ethylene oxide, the specific form of the promoter on the catalyst may be unknown. Examples of solid promoter compositions and their characteristics as well as methods for incorporating the promoters as part of the catalyst are described in Thorsteinson et al., U.S. Pat. No. 5,187,140, particularly at columns 11 through 15, Liu, et al., U.S. Pat. No. 6,511,938, Chou et al., U.S. Pat. No. 5,504,053, Soo, et al., U.S. Pat. No. 5,102,848, Bhasin, et al., U.S. Pat. Nos. 4,916,243, 4,908,343, and 5,059,481, and Lauritzen, U.S. Pat. Nos. 4,761,394, 4,766,105, 4,808,738, 4,820,675 and 4,833,261, all incorporated herein by reference. The solid promoters are generally added as chemical compounds to the catalyst prior to its use. As used herein, the term "compound" refers to the combination of a particular element with one or more different elements by surface and/or chemical bonding, such as ionic and/or covalent and/or coordinate bonding. The term "ionic" or "ion" refers to an electrically charged chemical moiety; "cationic" or "cation" being positive and "anionic" or "anion" being negative. The term "oxyanionic" or "oxyanion" refers to a negatively charged moiety containing at least one oxygen atom in combination with another element. An oxyanion is thus an oxygen-containing anion. It is understood that ions do not exist in vacuo, but are found in combination with charge-balancing counter ions when added as a compound to the catalyst. Once in the catalyst, the form of the promoter is not always known, and the promoter may be present without the counterion added during the preparation of the catalyst. For example, a catalyst made with cesium hydroxide may be analyzed to contain cesium but not hydroxide in the finished catalyst. Likewise, compounds such as alkali metal oxide, for example cesium oxide, or transition metal oxides, for example $MoO_3$, while not being ionic, may convert to ionic compounds during catalyst preparation or in use. For the sake of ease of understanding, the solid promoters will be referred to in terms of cations and anions regardless of their form in the catalyst under operating conditions.

The catalyst used in the methods of the present invention comprises a rhenium promoter, which can be provided in various forms, for example, as the metal, as a covalent compound, as a cation or as an anion. Rhenium promoted supported silver containing catalysts are known from U.S. Pat. No. 4,761,394 and U.S. Pat. No. 4,766,105, which are incorporated herein by reference. Broadly, the catalysts comprise silver, rhenium or compound thereof, and in some embodiments, a co-promoter such as a further metal or compound thereof and optionally an additional co-promoter such as one or more of sulfur, phosphorus, boron, and compounds thereof, on the support material. The rhenium species that provides the enhanced efficiency and/or activity is not certain and may be the component added or that generated either during preparation of the catalyst or during use as a catalyst. Examples of rhenium compounds include the rhenium salts such as rhenium halides, the rhenium oxyhalides, the rhenates, the perrhenates, the oxides and the acids of rhenium. However, the alkali metal perrhenates, ammonium perrhenate, alkaline earth metal perrhenates, silver perrhenates, other perrhenates and rhenium heptoxide can also be suitably utilized. Rhenium heptoxide, $Re_2O_7$, when dissolved in water, hydrolyzes to perrhenic acid, $HReO_4$, or hydrogen perrhenate. Thus, for purposes of this specification, rhenium heptoxide can be considered to be a perrhenate, that is, $ReO_4$. Similar chemistries can be exhibited by other metals such as molybdenum and tungsten.

The supported silver catalyst can comprise a rhenium promoter, a first co-promoter, and a second co-promoter; where the quantity of the rhenium promoter deposited on the carrier is greater than 1 mmole/kg (about 186 ppmw), relative to the weight of the catalyst; where the first co-promoter is selected from sulfur, phosphorus, boron, and mixtures thereof; where the second co-promoter is selected from tungsten, molybdenum, chromium, and mixtures thereof; and the total quantity of the first co-promoter and the second co-promoter deposited on the carrier is at most 3.8 mmole/kg, relative to the weight of the catalyst.

The catalyst can comprise a support and, deposited on the support, silver, a rhenium promoter, a first co-promoter, and a second co-promoter; wherein the molar ratio of the first co-promoter to the second co-promoter is greater than 1, wherein the first co-promoter is selected from sulfur, phosphorus, boron, and mixtures thereof; and wherein the second co-promoter is selected from tungsten, molybdenum, chromium, and mixtures thereof.

In some instances, the promoter comprises a mixture of cations, for example cesium and at least one other alkali metal, to obtain a synergistic efficiency enhancement as described in U.S. Pat. No. 4,916,243, herein incorporated by reference.

The concentration of the alkali metal promoters in the finished catalyst is not narrow and may vary over a wide range. The optimum alkali metal promoter concentration for a particular catalyst, given the other carrier and catalyst properties, will be dependent upon performance characteristics, such as catalyst efficiency, rate of catalyst aging and reaction temperature.

The concentration of alkali metal (based on the weight of cation, for example cesium) in the finished catalyst may vary from about 0.0005 to 1.0 wt. %, preferably from about 0.005 to 0.5 wt. %. The preferred amount of cation promoter deposited on or present on the surface of the support or catalyst generally lies between about 10 ppm and about 4000 ppm, preferably about 15 ppm and about 3000 ppm, and more preferably between about 20 ppm and about 2500 ppm by weight of cation calculated on the total support material. Amounts between about 50 ppm and about 2000 ppm are frequently most preferable. When the alkali metal cesium is used in mixture with other cations, the ratio of cesium to any other alkali metal and alkaline earth metal salt(s), if used, to achieve desired performance is not narrow and may vary over a wide range. The ratio of cesium to the other cation promoters may vary from about 0.0001:1 to 10,000:1, preferably from about 0.001:1 to 1,000:1.

Examples of some of the anion promoters or co-promoters which may be employed with the present invention include the halides, for example fluorides and chlorides, and the oxyanions of the elements other than oxygen having an atomic number of 5 to 83 of Groups 3b to 7b and 3a to 7a of the Periodic Table. One or more of the oxyanions of nitrogen, sulfur, manganese, tantalum, molybdenum, tungsten and rhenium may be preferred for some applications.

The types of anion promoters, co-promoters or modifiers suitable for use in the catalysts of this invention comprise, by way of example only, oxyanions such as sulfate, $SO_4^{-2}$, phosphates, for example, $PO_4^{-3}$, titanates, e.g., $TiO_3^{-2}$, tantalates, for example, $Ta_2O_6^{-2}$, molybdates, for example, $MoO_4^{-2}$, vanadates, for example, $V_2O_4^{-2}$, chromates, for example, $CrO_4^{-2}$, zirconates, for example, $ZrO_3^{-2}$, polyphosphates, manganates, nitrates, chlorates, bromates, borates, silicates, carbonates, tungstates, thiosulfates, cerates and the like. The halides may also be present, including fluoride, chloride, bromide and iodide.

It is well recognized that many anions have complex chemistries and may exist in one or more forms, for example, orthovanadate and metavanadate; and the various molybdate oxyanions such as $MoO_4^{-2}$, and $Mo_7O_{24}^{-6}$ and $Mo_2O_7^{-2}$. The oxyanions may also include mixed metal-containing oxyanions including polyoxyanion structures. For instance, manganese and molybdenum can form a mixed metal oxyanion. Similarly, other metals, whether provided in anionic, cationic, elemental or covalent form may enter into anionic structures.

While an oxyanion, or a precursor to an oxyanion, may be used in solutions for impregnating the support, it is possible that during the conditions of preparation of the catalyst and/or during use, the particular oxyanion or precursor initially present may be converted to another form. Indeed, the element may be converted to a cationic or covalent form. In many instances, analytical techniques may not be sufficient to precisely identify the species present. The invention is not intended to be limited by the exact species that may ultimately exist on the catalyst during use.

Another class of promoters, which may be employed with the present invention, includes manganese components. In many instances, manganese components can enhance the activity, efficiency and/or stability of catalysts. The manganese species that provides the enhanced activity, efficiency and/or stability is not certain and may be the component added or that generated either during catalyst preparation or during use as a catalyst. Manganese components include, but are not limited to, manganese acetate, manganese ammonium sulfate, manganese citrate, manganese dithionate, manganese oxalate, manganous nitrate, manganous sulfate, and manganate anion, for example permanganate anion, and the like. To stabilize the manganese component in certain impregnating solutions, it may be necessary to add a chelating compound such as ethylenediaminetetraacetic acid (EDTA) or a suitable salt thereof.

The amount of anion promoter may vary widely, for example, from about 0.0005 weight percent to about 2 weight percent, preferably from about 0.001 weight percent to about 0.5 weight percent based on the total weight of the catalyst. When used, the rhenium component is often provided in an amount of at least about 180 ppmw, say, to about 2000 ppmw, often between about 180 ppmw and 1000 ppmw, calculated as the weight of rhenium based on the total weight of the catalyst. In some embodiments, the rhenium component is provided in an amount of at least about 270 ppmw, at least about 360 ppmw.

It is desirable that the silver, the rhenium promoter and/or one or more additional promoters and/or co-promoters be relatively uniformly dispersed on the support. A preferred procedure for depositing silver catalytic material, rhenium and one or more promoters comprises: (1) impregnating a support according to the present invention with a solution comprising a solvent or solubilizing agent, silver complex and one or more promoters, and (2) thereafter treating the impregnated support to convert the silver compound and effect deposition of silver and the promoters) onto the exterior and interior pore surfaces of the support. Silver and promoter depositions are generally accomplished by heating the solution containing support at elevated temperatures to evaporate the liquid within the support and effect deposition of the silver and promoters onto the interior and exterior support surfaces. The temperature of the heating step is high enough to reduce any silver compounds to metallic silver. Impregnation of the support is the preferred technique for silver deposition because it utilizes silver more efficiently than coating procedures, the latter being generally unable to effect substantial silver deposition onto the interior surfaces of the support. In addition, coated catalysts are more susceptible to silver loss by mechanical abrasion.

Well known methods can be employed to analyze for the amounts of silver, promoter and co-promoters deposited onto the alpha-alumina support. The skilled artisan may employ, for example, material balances to determine the amounts of any of these deposited components. Alternatively, any suitable analytical technique for determining elemental composition, such as X-ray fluorescence (XRF), may be employed to determine the amounts of the deposited components.

The gaseous chlorine-containing promoter species introduced in the reaction mixture are also otherwise termed as gas-phase modifiers, inhibitors and/or enhancers. Suitable gaseous chlorine-containing promoter species can be selected from a group containing C1-C8 chlorohydrocarbons. Exemplary chlorohydrocarbons include ethyl chloride, vinyl chloride, ethylene dichloride, methyl chloride and any mixtures thereof. Ethyl chloride and ethylene dichloride are most preferred. Using gaseous chlorine-containing promoter species as an example, it is believed that the ability of the gaseous chlorine-containing promoter species to enhance the efficiency and/or activity of the epoxidation process depends on the extent to which the gaseous chlorine-containing promoter species chlorinates the surface of the catalyst, for example, by depositing particular chlorine species such as atomic chlorine or chloride ions on the catalyst. However, hydrocarbons lacking chlorine atoms are believed to strip chlorides from the catalyst, and therefore, detract from the overall efficiency enhancement provided by the gaseous chlorine-containing promoter species. Discussions of this phenomenon may be found in Berty, "Inhibitor Action of Chlorinated Hydrocarbons in the Oxidation of Ethylene to Ethylene Oxide," Chemical Engineering Communications, Vol. 82 (1989) at 229-232 and Berty, "Ethylene Oxide Synthesis," Applied Industrial Catalysis, Vol. I (1983) at 207-238. Paraffinic compounds, such as ethane or propane, are believed to be especially effective at stripping chlorides from the catalyst. However, olefins such as ethylene and propylene, are also believed to act to strip chlorides from the catalyst. Some of these hydrocarbons may also be introduced as impurities in the alkylene feed or may be present for other reasons (such as the use of recycle stream) in the reaction mixture. Typically, the preferred concentration of ethane in the reaction mixture, when present, is from 0 to about 2 mole percent. Given the competing effects of the gaseous chlorine-containing promoter species and the non-halogenated, chloride-removing hydrocarbons in reaction mixture, it is convenient to define an "overall catalyst chloriding effectiveness value" that represents the net effect of the promoting and chloride-removing gas phase species in chloriding the catalyst. In the case of gaseous chlorine-containing promoter species, the "overall catalyst chloriding effectiveness" value can be defined as the dimensionless quantity $Z^*$ and represented by the following formula (III):

$$Z^* = \frac{\text{ethyl chloride equivalent } (ppmv)}{\text{ethane equivalent (mole percent)}} \quad \text{(III)}$$

wherein the ethyl chloride equivalent is the concentration in ppmv of ethyl chloride that provides substantially the same catalyst chloriding effectiveness of the gaseous chlorine-containing promoter species present in the reaction mixture at the concentrations of the gaseous chlorine-containing promoter species in the reaction mixture; and the ethane equivalent is the concentration of ethane in mole percent that provides substantially the same catalyst dechloriding effectiveness of the non-chloride containing hydrocarbons in the reaction mixture at the concentrations of the non-chloride containing hydrocarbons in the reaction mixture.

If ethyl chloride is the only gaseous chlorine-containing promoter species present in the reaction mixture, the ethyl chloride equivalent (i.e., the numerator in equation (III)) is the ethyl chloride concentration in ppmv. If other gaseous chlorine-containing promoter species (specifically vinyl chloride, methyl chloride or ethylene dichloride) are used alone or in conjunction with ethyl chloride, the ethyl chloride equivalent is the concentration of ethyl chloride in ppmv plus the concentrations of the other gaseous chlorine-containing promoter species (corrected for their effectiveness as a promoter as compared to ethyl chloride). The relative effectiveness of a non-ethyl chloride promoter can be measured experimentally by replacing ethyl chloride with the other promoter and determining the concentration needed to obtain the same level of catalyst performance provided by ethyl chloride. As a way of further illustration, if the required concentration of ethylene dichloride at the reactor inlet is 0.5 ppmv to realize equivalent effectiveness in terms of catalyst performance provided by 1 ppmv of ethyl chloride, then the ethyl chloride equivalent for 1 ppmv ethylene dichloride would be 2 ppmv ethyl chloride. For a hypothetical feed having 1 ppmv ethylene dichloride and 1 ppmv ethyl chloride, the ethyl chloride equivalent in the numerator of $Z^*$ would then be 3 ppmv. As a further example, it has been found that methyl chloride has about 10 times less the chloriding effectiveness of ethyl chloride. Therefore, the ethyl chloride equivalent for a given concentration of methyl chloride in ppmv is 0.1× (methyl chloride concentration in ppmv). It has also been found that for certain catalysts, vinyl chloride has the same chloriding effectiveness as ethyl chloride. Therefore, for such catalysts the ethyl chloride equivalent for a given concentration of vinyl chloride in ppmv is 1.0× (vinyl chloride concentration in ppmv). When more than two chlorine-containing promoters are present in reaction mixture, which is often the case in commercial ethylene epoxidation processes, the overall ethyl chloride equivalent is the sum of the corresponding ethyl chloride equivalents for each individual chlorine-containing promoter that is present. As an example, for a hypothetical feed of 1 ppmv ethylene dichloride, 1 ppmv ethyl chloride, and 1 ppmv vinyl chloride, the ethyl chloride equivalent in the numerator of $Z^*$ would be 2*1+1+1*1=4 ppmv.

The ethane equivalent (i.e., the denominator in equation (III)) is the concentration of ethane in mole percent in the reaction mixture plus the concentration of the other hydrocarbons effective in removing chloride from the catalysts, corrected for their effectiveness for dechlorination relative to ethane. The relative effectiveness of ethylene and ethane can be measured experimentally by determining the inlet ethyl chloride equivalent concentration that provides the same level of catalyst performance for a feed comprising both ethylene and ethane as compared to the same feed with the same ethylene concentration but a specific ethyl chloride equivalent concentration and no ethane. As a way of further illustration, if with a reaction mixture composition comprising an ethylene concentration of 30.0 mole percent and an ethane concentration of 0.30 mole percent, a level of 6.0 ppmv ethyl chloride equivalents is found to provide the same level of catalyst performance as 3.0 ppmv ethyl chloride equivalents with a similar reaction mixture composition but lacking ethane, then the ethane equivalent for 30.0 mole percent ethylene would be 0.30 mole percent. For a reaction mixture having 30.0 mole percent ethylene and 0.3 mole percent ethane, the ethane equivalent will then be 0.6 mole percent. As another illustration, it has been found that for certain catalysts methane has about 500 times less the dechloriding effectiveness of ethane. Thus, for such catalysts the ethane equivalent for methane is 0.002× (methane concentration in mol %). For a typical reaction mixture having 30.0 mole percent ethylene and 0.1 mole percent ethane, the ethane equivalent then will be 0.4 mole percent. The relative effectiveness of hydrocarbons other than ethane and ethylene can be measured experimentally by determining the inlet ethyl chloride equivalent concentrations required to achieve the same catalyst performance for a reaction mixture comprising the hydrocarbon of interest at its feed concentration at two different feed ethane concentrations. If a hydrocarbon compound is found to have a very small dechloriding effect and is also present in low concentrations, then its contribution to the ethane equivalent concentration in the $Z^*$ calculation will be negligible.

Thus, given the foregoing relationships, in the case where the reaction mixture includes ethylene, ethyl chloride, ethylene dichloride, vinyl chloride, and ethane, the overall catalyst chloriding effectiveness value can be defined by equation (IV):

$$Z^* = \frac{(ECL + (2 \times EDC) + VCL)}{(C_2H_6 + (0.01 \times C_2H_4))} \qquad (IV)$$

wherein ECL, EDC, and VCL are the concentrations in ppmv of ethyl chloride ($C_2H_5Cl$), ethylene dichloride (Cl—$CH_2$—$CH_2$—Cl), and vinyl chloride ($H_2C=CH$—Cl), respectively, in the reaction mixture. $C_2H_6$ and $C_2H_4$ are the concentrations in mole percent of ethane and ethylene, respectively, in the reaction mixture. It is important that the relative effectiveness of the gaseous chlorine-containing promoter species and the hydrocarbon dechlorinating species also be measured under the conditions at which the epoxidation reaction is performed. $Z^*$ will preferably be maintained at a level that is no greater than about 20 and which is most preferably no greater than about 15. $Z^*$ is preferably at least about 1.

Although the gaseous chlorine-containing promoter species may be supplied as a single species, upon contact with the catalyst, other species may be formed leading to a mixture in the outlet stream of the reactor. In some embodiments, the reaction mixture can include a recycle feed stream from the reactor. Consequently, if the outlet stream of the reactor is recycled, a mixture of species will be found in the reaction mixture. As used herein the term "reaction mixture" means the reactor inlet feed gas, which includes alkylene, oxygen and a gaseous chlorine-containing promoter species, as well as the recycle feed stream to the reactor, if present. In particular, the recycle feed stream to the reactor may contain ethyl chloride, vinyl chloride, ethylene dichloride and/or methyl chloride, even though only ethyl chloride or ethylene dichloride is supplied to the system. The concentrations of ethyl chloride, vinyl chloride, and ethylene dichloride must be considered in calculating $Z^*$.

Typically, the outlet stream from the reactor contains dilute concentrations of alkylene oxide along with unreacted alkylene, unreacted oxygen, aldehydes, acidic impurities, nitrogen, argon and carbon dioxide among others. Carbon dioxide is produced as a reaction by-product and may also be introduced with other inlet reaction gases as an impurity. The alkylene oxide can be separated and recovered from the outlet stream of the reactor. The remaining material in the outlet stream of the reactor can be recycled back to the reactor as a recycle feed stream to diminish loss of unreacted alkylene. In some embodiments, the outlet stream of the reactor can be passed through a carbon dioxide removal unit to remove and/or minimize the amount of carbon dioxide prior to introducing in the reactor as the recycle feed stream. In one embodiment, the carbon dioxide concentration in the recycle feed stream is no more than about 5 mole percent, and more preferably no more than about 3 mole percent and even more preferably no more than about 2 mole percent of the total composition of the reaction mixture. Water may also be present in the recycle feed stream in concentrations that are preferably from about 0 mole percent to no more than about 3 mole percent.

In one embodiment, the epoxidation reaction is operated at the preferred operating condition over a period yielding a production of at least about 250 kmole alkylene oxide per cubic meter (kmole $m^{-3}$) of the catalyst, where the volume of the catalyst is measured as the packed volume of the reactor. In some embodiments, the epoxidation reaction is operated at the preferred operating condition over a period yielding a production of at least about 500 kmole alkylene oxide per cubic meter of the catalyst. In another embodiment, the epoxidation reaction is operated at the preferred operating condition over a period yielding a production of at least about 1000 kmole alkylene oxide per cubic meter of the catalyst. The "packed volume of the reactor" is the volume of the reactor that is actually occupied by the catalyst bed.

In a preferred embodiment, the epoxidation reaction is operated at the preferred operating condition prior to reaching a cumulative alkylene oxide production of about 50000 kmole $m^{-3}$ of catalyst (where the volume of the catalyst is measured as the packed volume of the reactor), preferably prior to reaching about 20000 kmole $m^{-3}$ of catalyst, and more preferably prior to reaching about 10000 kmole $m^{-3}$ of catalyst.

The preferred operating condition can be determined from a derivative of efficiency to productivity of the epoxidation reaction. The method involves determining a derivative of efficiency to productivity of the epoxidation reaction as a function of the overall catalyst chloriding effectiveness value ($Z^*$) at a first temperature, with the other components of the operating conditions remaining substantially unchanged. The derivative of efficiency to productivity of the epoxidation reaction is in a range of about −1 to about −4 when efficiency of the epoxidation reaction is expressed in percent and productivity of the epoxidation reaction is expressed as the concentration of alkylene oxide in mole percent in a reactor outlet stream. The overall catalyst chloriding effectiveness may be varied by changing the concentration of one or more gaseous chlorine-containing promoter species and/or the concentration of one or more non-chlorine containing hydrocarbon species and it is most preferred that the concentration of alkylene is not varied. (One of skill in the art will appreciate that the concentration of alkylene may be varied but doing so will require making appropriate adjustments in the calculations.) In one embodiment, the derivative is measured using a slope-based method. For example, the efficiency and associated productivity of the epoxidation reaction are measured at a first overall catalyst chloriding effectiveness value to obtain a first efficiency value and a first productivity value at the first temperature. At a second overall catalyst chloriding effectiveness value, the epoxidation reaction provides a second efficiency value and a second productivity value at the first temperature. According to embodiments of the present invention, the preferred operating condition is characterized by the slope, where the slope is obtained from the difference between the first efficiency value and the second efficiency value divided by the difference between the first productivity value and the second productivity value. The slope has a value of between about −1 to about −4, when efficiency is expressed in percent and productivity as mole percent of alkylene oxide contained in a reactor outlet stream. In some embodiments, the preferred operating condition is characterized by the second efficiency value and the corresponding second productivity value which can be determined from the slope. For example, once a first productivity value and corresponding first efficiency value for an epoxidation reaction is known at the first temperature, the reaction can be operated at the preferred operating condition, which is characterized by the second efficiency value and the second productivity value at the first temperature, by changing an overall catalyst chloriding effectiveness until the slope is between about −1 and about −4, when efficiency is expressed in percent and productivity as mole percent of alkylene oxide in a reactor outlet stream.

FIG. 1 is a flowchart 10 of a method of determining the preferred operating condition of an epoxidation reaction according to some embodiments of the present invention. At step 12, a first data set of efficiency and productivity of the epoxidation reaction at a first temperature is generated. The first data set includes efficiency values associated with at least three overall catalyst chloriding effectiveness values at the first temperature and the corresponding productivity values, with other components of the operating conditions remaining substantially unchanged. The at least three overall catalyst chloriding effectiveness values correspond to three different overall catalyst chloriding effectiveness values and are obtained by varying the concentration of one or more gaseous chlorine-containing promoter species and/or the concentration of one or more non-chlorine containing hydrocarbon species, and it is most preferred that the concentration of alkylene is not varied. It is preferred that the overall catalyst chloriding effectiveness is varied by changing the inlet concentration of one or more gaseous chlorine-containing promoter species and/or the inlet concentration of one or more saturated non-chlorine containing hydrocarbons. It is most preferred that the overall catalyst chloriding effectiveness is changed by changing the inlet concentration of a gaseous chlorine-containing promoter species, for example, by changing its feed rate to the reactor. When $Z^*$ is employed as the measure of overall catalyst chloriding effectiveness, the at least three overall catalyst chloriding effectiveness values can be between about 1 and 30. The at least three overall catalyst chloriding effectiveness values can include a low value, one or more medium values and a high value, and these values may change with temperature, as well as with the higher overall catalyst chloriding effectiveness values generally associated with higher temperatures. It is also desirable that at least one of the one or more medium values is associated with the highest efficiency when compared to the efficiencies obtained at the low and the high overall catalyst chloriding effectiveness values. If the highest efficiency is obtained at the one or both of these overall catalyst chloriding effectiveness values, that is the low and/or high values, then it is preferred to generate additional data on efficiency and productivity of the epoxidation reaction at still lower and/or higher overall catalyst chloriding effectiveness values than the low value and/or the high value, respectively. In one embodiment, at a reactor temperature of about 240° C., the low value of $Z^*$ is about 1 to about 2, the one or more medium values of $Z^*$ are about 2 to about 3, and the high value of $Z^*$ is about 3 to about 4.

The first temperature is selected such that the temperature falls within the temperature range of the epoxidation reaction, as described previously. In some embodiments, the first temperature is preferably at least about 200° C., more preferably at least about 210° C., and most preferably at least about 220° C. The first temperature is not more than about 300° C., more preferably not more than about 290° C., and most preferably not more than about 280° C. Typically, the productivity of the epoxidation reaction over the selected range of overall catalyst chloriding effectiveness values at the first temperature is greater than about 1 mole percent of alkylene oxide when expressed as molar concentration in the outlet stream. In certain embodiments, the productivity of the epoxidation reaction over the selected range of overall catalyst chloriding effectiveness values at the first temperature is in a range of about 1 mole percent to about 4 mole percent alkylene oxide. In some embodiments, the maximum efficiency of the epoxidation reaction over the selected range of overall catalyst chloriding effectiveness values at the first temperature is at least about 85 percent. In certain embodiments, the maximum efficiency of the epoxidation reaction over the selected range of overall catalyst chloriding effectiveness values at the first temperature is in a range of about 85 percent to about 95 percent.

A maximum efficiency value at the first temperature is determined, at step 14, from the first data set, and corresponds to a maximum efficiency achievable at the first temperature by varying the overall catalyst chloriding effectiveness. In some embodiments, determining a maximum efficiency value at the first temperature includes generating a plot, or using a program, or using a mathematical equation or any combinations thereof. As known to those skilled in the art, increasing the number of data points of the first data set may improve the quality of determining a maximum efficiency value. As will be appreciated, increasing the number of data points involves generating data at more than three overall catalyst chloriding effectiveness values at the first temperature, and/or repeating measurements at least some of the at least three overall catalyst chloriding effectiveness values at the first temperature.

At step 16, a range of efficiency values lower than the maximum efficiency value is selected. According to embodiments of the present invention, the range of efficiency values corresponds to the preferred operating condition and is further characterized by higher productivity of the epoxidation reaction than that achievable when the reaction is performed at the maximum efficiency value at the first temperature. In some embodiments, the range of efficiency values is marked by productivity values of at least about 1 percent greater than that obtained at the maximum efficiency value, that is, at least about 1.01 times the concentration of alkylene oxide in the reactor outlet stream corresponding to the maximum efficiency value. In certain embodiments, the range of efficiency values is marked by productivity values of at least about 5 percent greater than that obtained at the maximum efficiency value, that is, at least about 1.05 times the concentration of alkylene oxide in the reactor outlet stream corresponding to the maximum efficiency value. In one embodiment, the range of efficiency values is marked by productivity values of at least about 10 percent greater than that obtained at the maximum efficiency value, that is, at least about 1.1 times the concentration of alkylene oxide in the reactor outlet stream corresponding to the maximum efficiency value.

A flowchart 20 of a method of determining the preferred operating condition of an epoxidation reaction according to one embodiment of the present invention is shown in FIG. 2. The flow chart 20 illustrates one particular method by which the flow chart 10 can be employed to determine the preferred operating condition. The flowchart 20 includes step 12, as discussed previously with reference to flowchart 10. A first data set of efficiency and productivity of the epoxidation reaction at a first temperature is generated, at step 12, at least three overall catalyst chloriding effectiveness values. At step 22, a first curve with a first maximum is generated, by plotting the first data set on a first plot. In some embodiments, the first data set can be fitted mathematically to generate a first curve. In one embodiment, the first curve can be generated by fitting first data set with a second order polynomial function to form a fitted curve, the fitted curve having the form of a downward opening parabola. In one embodiment, the abscissa (X-axis) of the first plot corresponds to the productivity of the epoxidation reaction at the at least three overall catalyst chloriding effectiveness values and the ordinate (Y-axis) of the first plot corresponds to the efficiency of the epoxidation reaction at the at least three overall catalyst chloriding effectiveness values. In embodiments where the ordinate of the first plot corresponds to the efficiency of the epoxidation reaction, reading the location of the first maximum along the vertical axis provides a maximum efficiency value (which is the maximum efficiency achievable by varying the overall catalyst chloriding effectiveness at the first temperature), and reading the location of the first maximum along the horizontal axis results in the corresponding productivity of the epoxidation reaction.

At step 24, a first region on the first curve is selected. According to embodiments of the present invention, the first region corresponds to the preferred operating condition at the first temperature and lies to the right of the first maximum when the abscissa of the first plot is the productivity of the epoxidation reaction. The first region is characterized by a range of efficiency values which is lower than the efficiency obtained at the first maximum. As will be appreciated, the loss in efficiency due to operating the epoxidation reaction at the first region is offset by the gain in productivity.

FIG. 3 is an illustration of a first plot 30 obtained by plotting a first data set of efficiency and productivity values at a first temperature using the method as shown in flowchart 20, in accordance with embodiments of the present invention. The first data set is obtained at overall catalyst chloriding effectiveness values of 2.5, 3.1, 3.7 and 4.4 with fixed inlet ethylene and ethane concentration targets of 30 and 0.5 mole percent, respectively, and at a temperature of 245° C. and is plotted to generate a first curve 34 with a first maximum 36 on the first plot. The first maximum 36 has corresponding efficiency and productivity values as referenced by the numerals 38 and 40, respectively. In this embodiment, the numeral 38 refers to the maximum efficiency value obtained at 245° C. and the numeral 40 refers to the corresponding productivity value. A first region 42 is selected which lies towards the right of the first maximum 36 when the abscissa of the first plot 30 is the productivity of the epoxidation reaction. In one embodiment, the first region 42 has a productivity that is at least about 1% greater than the productivity 40 corresponding to the first maximum 36 (at least 1.01 times productivity 40). In some embodiments, the first region 42 has a productivity that is at least about 5% greater than the productivity 40 corresponding to the first maximum 36 (at least 1.05 times productivity 40). In certain embodiments, the first region 42 has a productivity that is at least about 10% greater than the productivity 40 corresponding to the first maximum 36 (at least 1.10 times productivity 40). As will be appreciated, the first region 42 corresponds to the region on the plot where the slope is between −1 and −4, when efficiency of the epoxidation reaction is expressed in percent and productivity of the epoxidation reaction is expressed as the concentration of alkylene oxide in mole percent in a reactor outlet stream.

Figure 4:
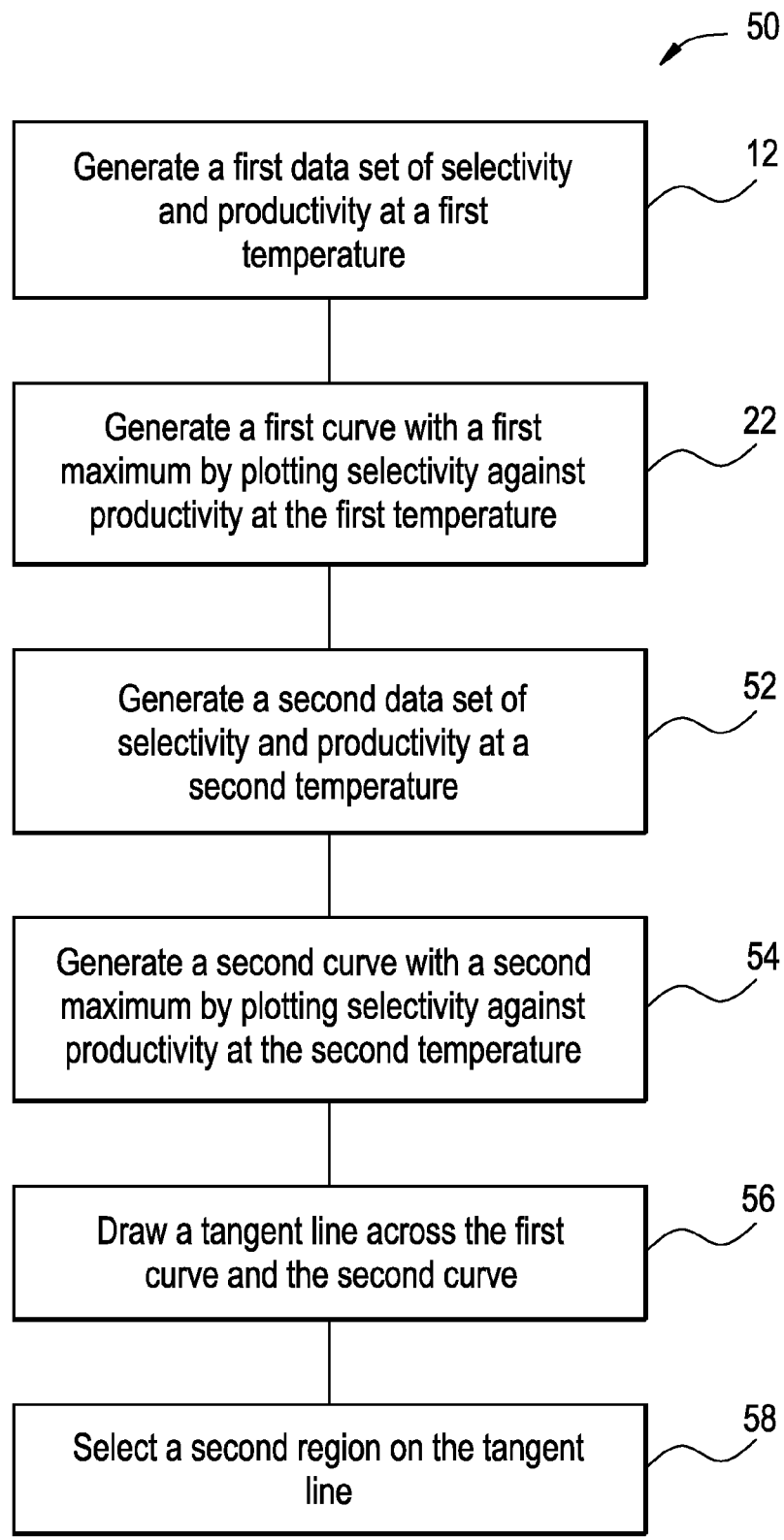
FIG. 4 is a flowchart of yet another method of determining a preferred operating condition according to embodiments of the present invention.

A flow chart 50 in accordance with embodiments of the present invention is provided in FIG. 4. The flow chart 50 includes steps 12 and 22, as discussed previously with reference to flow chart 20 of FIG. 2. At step 52, a second data set on efficiency and productivity of the epoxidation reaction is generated at a second temperature. The second data set includes efficiency values associated with at least three overall catalyst chloriding effectiveness values at the second temperature and the corresponding productivity values, with other components of the operating conditions remaining substantially unchanged. The second temperature can be lower or higher than the first temperature. It is desirable to have an incremental increase or decrease from the first temperature to attain the second temperature. In some embodiments, the second temperature is different from the first temperature by greater than about 1 degree Celsius. In certain embodiments, the second temperature is different from the first temperature by greater than about 3 degrees Celsius. In one embodiment, the second temperature is different from the first temperature by greater than about 5 degrees Celsius.

In some embodiments, the at least three overall catalyst chloriding effectiveness values employed for generating the second data set, at step 52, can be the same as employed for generating the first data set, at step 12. In certain embodiments, the at least three overall catalyst chloriding effectiveness values used in step 52 can be different from those employed for generating the first data set. The at least three overall catalyst chloriding effectiveness values used in step 52 include a low value, one or more medium values and a high value, as mentioned previously with regard to step 12. The at least three overall catalyst chloride effectiveness values used in step 52 are obtained as described with regard to step 12, above.

At step 54, a second curve is generated by platting the second data set on the first plot. The second curve is characterized by a second maximum, where the efficiency shows a maximum at the second temperature. In embodiments where the second temperature is higher than the first temperature, the second curve may typically shift towards the lower right of the first curve, to greater productivity values and lower efficiency values. In embodiments where the second temperature is lower than the first temperature, the second curve may shift towards the upper left of the first curve.

A tangent line can be drawn across the first curve and the second curve, at step 56. The tangent line touches the first curve and the second curve at points that lie towards the right of the first maximum and the second maximum. According to embodiments of the present invention, when the tangent line is constructed as described above, a slope of the tangent line is found to be in a range of about −1 to about −4, when efficiency is expressed in percent and productivity as mole percent of alkylene oxide in the reactor outlet stream. The slope of the resulting tangent line may vary within this range depending on factors such as temperature, reactor conditions and/or catalyst age.

A second region can be selected at step 58. The second region lies on the tangent line and corresponds to the preferred operating condition according to embodiments of the present invention.

As will be appreciated, a preferred operating condition yielding a desired productivity can be determined from the tangent line drawn across the first curve and the second curve.

In one embodiment, the desired productivity is achieved at a point on the tangent line that lies between the points of tangency with the first curve at first temperature and the second curve at second temperature. In embodiments where the desired productivity is higher or lower than both the productivity at the tangent point for the first curve at the first temperature and the productivity at the tangent point for the second curve at the second temperature, the tangent line can be extrapolated to obtain the preferred operating condition. In one embodiment, the temperature ($T_3$) and overall catalyst chloriding effectiveness value ($Z_3^*$) corresponding to the preferred operating condition can be determined using equations (V and VI) as given below:

$$T_3 = T_1 + \left[\frac{(T_2 - T_1)}{(C_{AO2} - C_{AO1})}\right] \times (C_{AO3} - C_{AO1}) \quad (V)$$

$$Z_3^* = Z_1^* + \left[\frac{(Z_2^* - Z_1^*)}{(C_{AO2} - C_{AO1})}\right] \times (C_{AO3} - C_{AO1}) \quad (VI)$$

where, $T_1$, $T_2$ and $T_3$ are the first temperature, second temperature, and third temperature, respectively; $C_{AO1}$ and $C_{AO2}$ are the concentrations of alkylene oxide in the outlet stream at the points where the tangent line meets the response curves at $T_1$ and $T_2$, respectively; $C_{AO3}$ is a desired level of productivity in mole percent in the outlet stream; $Z_1^*$ and $Z_2^*$ are the overall catalyst chloriding effectiveness values at the points where the tangent line meets the response curves at $T_1$ and $T_2$, respectively, and may be determined if required by interpolation or extrapolation from a plot of outlet alkylene oxide concentration against the overall catalyst chloriding effectiveness values at $T_1$ and $T_2$, respectively; and $Z_3^*$ is the overall catalyst chloriding effectiveness value corresponding to the preferred operating condition at the third temperature.

In one embodiment, the steps 12-58 of the flow chart 50 can be repeated to obtain more than two curves at more than two temperatures with the associated efficiency and productivity values. A tangent line, or a series of tangent lines, or a smoothly varying tangent curve drawn across the more than two curves can provide the preferred operating condition in a manner similar to that described above at each of the temperatures.

Figure 5:
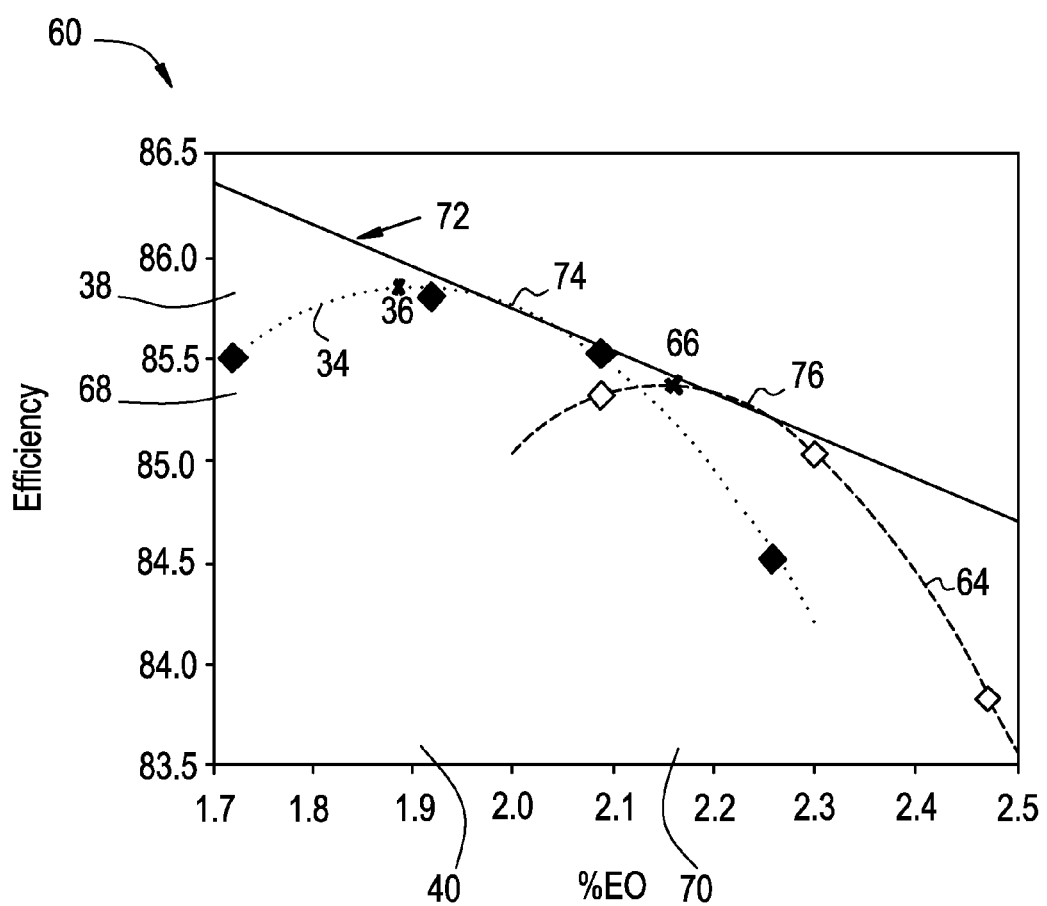
FIG. 5 is an illustration of a plot of efficiency against productivity of an epoxidation reaction obtained using the method shown in FIG. 4, in accordance with embodiments of the present invention.

FIG. 5 is an illustration of a plot 60 of the first data set and the second data set obtained using the flowchart 50, in accordance with embodiments of the present invention. The first data set can be plotted to get the first curve 34 with the first maximum 36, as described with reference to FIG. 3. The corresponding efficiency and productivity values are referred by the numerals 38 and 40, respectively. A plot of the second data set at 250° C. with overall catalyst chloriding effectiveness values of 3.6, 4.4 and 5.0, at fixed inlet ethylene and ethane concentration targets of 30 and 0.5 mole percent, respectively, provides a second curve 64 with a second maximum 66 and the corresponding efficiency and productivity values are referred by the numerals 68 and 70, respectively. A tangent line 72 is drawn across the first curve 34 and the second curve 64. The tangent line 72 touches the first curve 34 and the second curve 64, at points marked by the numerals 74 and 76, as shown in the FIG. 5. The points 74 and 76 lie towards the right of the first maximum 36 and second maximum 66 of the first curve 34 and the second curve 64, respectively. The preferred operating condition at the first temperature corresponds to the region on the first curve that touches the tangent line 72, as marked by 74, and for the second temperature it corresponds to point 76, according to embodiments of the present invention.

Figure 6:
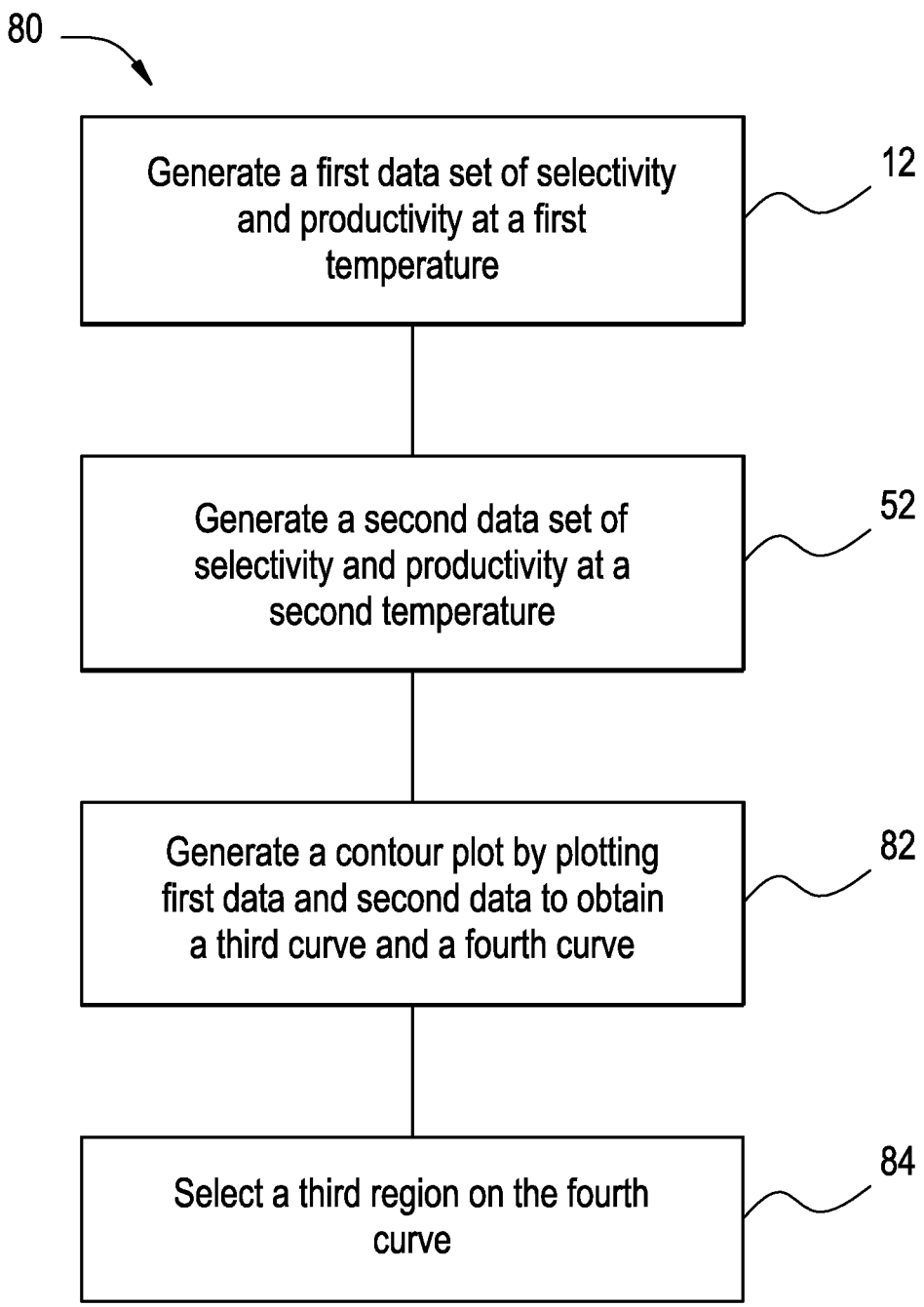
FIG. 6 is a flowchart of a method of determining a preferred operating condition according to embodiments of the present invention.

A flow chart 80 of a method according to embodiments of the present invention is shown in FIG. 6. The flow chart 80 includes steps 12 and 52 as shown in the flow chart 50 of FIG. 4. At step 12, a first data set of efficiency and productivity of the epoxidation reaction at the at least three overall catalyst chloriding effectiveness values at the first temperature is generated. At step 52, a second data set of efficiency and productivity of the epoxidation reaction at the at least three overall catalyst chloriding effectiveness values at the second temperature is generated.

At step 82, a contour plot is generated by plotting the first data set and the second data set. In one embodiment, the first data set and the second data set are plotted as functions of overall catalyst chloriding effectiveness value and temperature to obtain at least one third curve and at least one fourth curve. The at least one third curve corresponds to a contour of constant efficiency of the epoxidation reaction, and the at least one fourth curve corresponds to a contour of constant productivity of the epoxidation reaction.

A third region on the contour plot is selected, at step 84. The third region corresponds to the preferred operating condition. In one embodiment, the third region lies on the at least one fourth curve corresponding to a desired level of productivity and is further characterized by the at least one third curve having highest efficiency and which also meets the at least one fourth curve of interest.

In some embodiments, steps 12 or 52 are repeated at a third temperature and the contour plot is generated by plotting data at least three temperatures. As will be appreciated, generating data at more than three temperatures can provide a determination of the preferred operating condition that is better in comparison with the contour plot generated at three temperatures.

Figure 7:
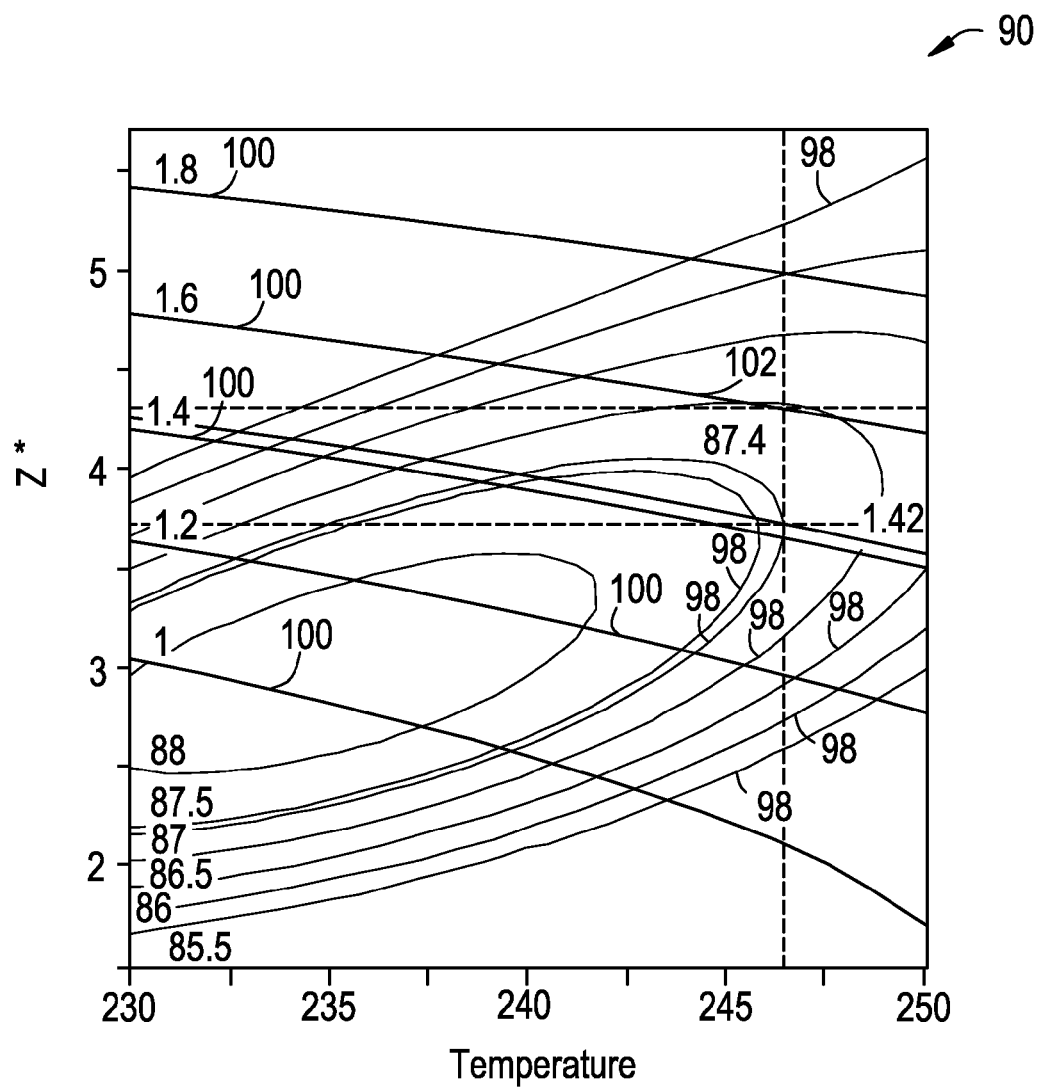
FIG. 7 is an illustration of a contour plot of efficiency and productivity as functions of overall catalyst chloriding effectiveness value and temperature, obtained using the method shown in FIG. 6, in accordance with embodiments of the present invention.

FIG. 7 is a contour plot 90 of a first data set, a second data set and a third data set obtained by following the method of flow chart 80. In this embodiment, the abscissa of the contour plot 90 is the temperature and the ordinate is the overall catalyst chloriding effectiveness value. From the first data set, the second data set and the third data set, the efficiency data at the three temperatures and at the at least three overall catalyst chloriding effectiveness values can be plotted on the contour plot 90 to obtain at least one third curve 98. The productivity values from the first data set, the second data set and the third data set can be plotted to obtain at least one fourth curve 100. The preferred operating condition can be determined by choosing the at least one fourth curve 100 and selecting the intersection of the at least one third curve 98 on the at least one fourth curve 100 which provides maximum efficiency at that productivity. In one embodiment, the temperature and the overall catalyst chloriding effectiveness value corresponding to the preferred operating condition can be read from the axes of the contour plot 90. In the illustrated embodiment of FIG. 7, for a desired productivity of 1.6% EO, a maximum efficiency of about 87% can be obtained at a temperature of 246.5° C. and an overall catalyst chloriding effectiveness value of about 4.3 $Z^*$. As will be appreciated, the efficiency of 87% at preferred operating condition 102 is lower than the maximum efficiency of 87.4% obtainable at the temperature of 246.5° C. with an overall catalyst chloriding effectiveness value of about 3.7 $Z^*$, where the productivity is about 1.42% EO.

Figure 8:
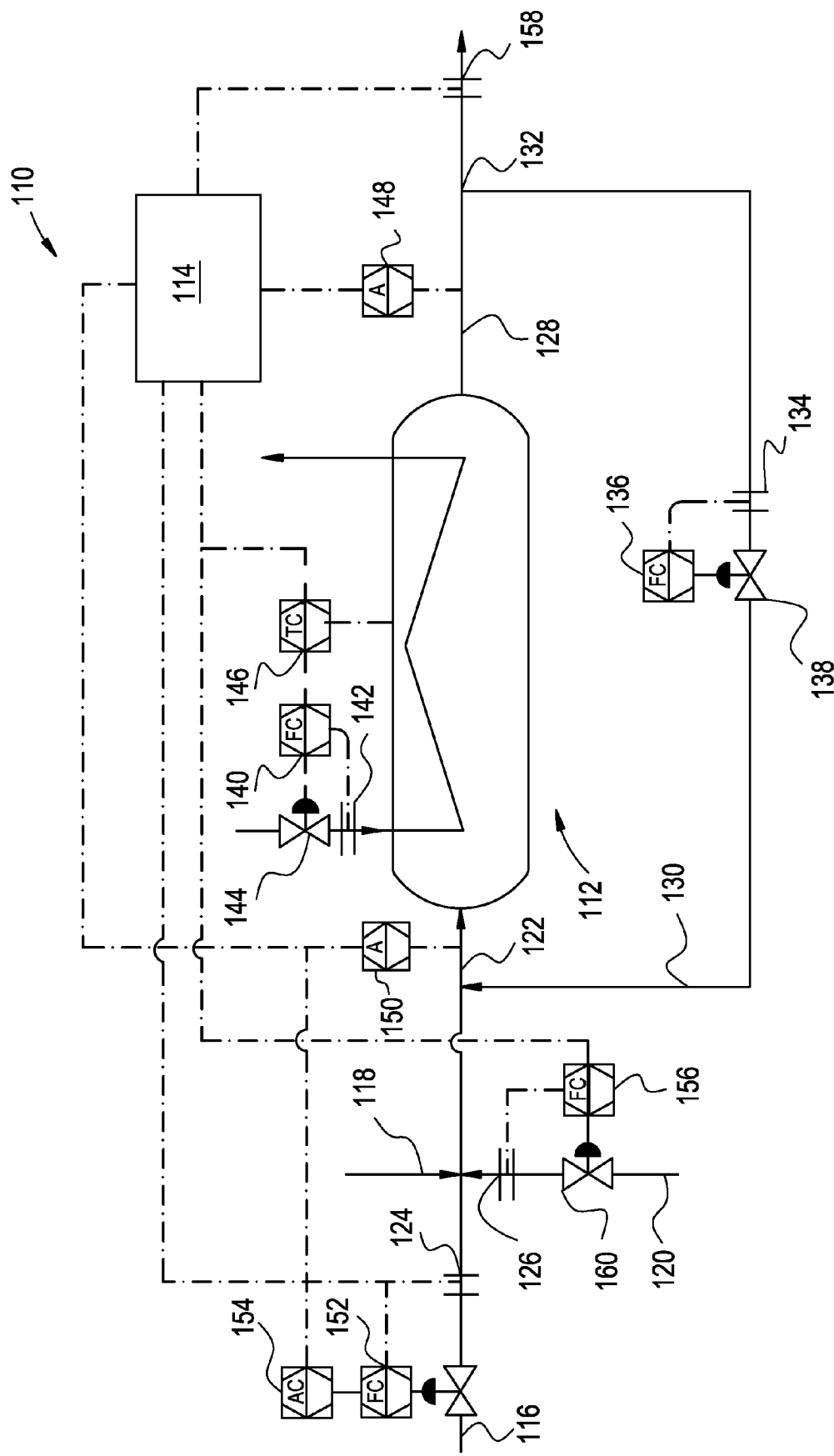
FIG. 8 is schematic diagram of a system for producing alkylene oxide according to embodiments of the present invention.

FIG. 8 is a schematic diagram of a system 110 according to embodiments of the present invention. The system 110 includes a reactor 112 and a controller 114. In the illustrated embodiment of FIG. 8, the reactor 112 is a tubular vessel with a catalyst bed disposed in it. An alkylene feed 116, an oxygen feed 118 and a gaseous chlorine-containing promoter species feed 120 are combined and is introduced into the reactor 112 as a reaction mixture 122. The numerals 124 and 126 depict the flow meters for the alkylene feed 116 and gaseous chlorine-containing promoter species feed 120, respectively. A reactor outlet stream 128 including alkylene oxide product, plus side products and/or impurities (e.g., $CO_2$, $H_2O$, and saturated hydrocarbons) and unreacted olefins and oxygen can be taken out from the reactor 112. If desired, a recycle feed stream 130 can be provided in the reactor 112 to recycle unreacted olefins and oxygen in the reactor outlet stream 128. The recycle feed stream 130 can include a flow meter 134 and a recycle flow controller 136. The recycle flow controller 136 receives recycle flow data from flow meter 134 and can manipulate control valve 138 to control the flow rate of recycle feed stream 130.

The temperature of the reactor 112 can be controlled by means of a coolant system, such as a boiling water-cooled system. A coolant pressure controller 140 receives coolant data from pressure meter 142 and adjusts coolant control valve 144 to change the coolant pressure and effect the temperature change. A reactor temperature controller 146 receives a temperature signal from a reactor thermocouple and provides an output that resets the set point of coolant pressure controller 140.

The controller 114 can receive inputs from a reactor outlet stream concentration analyzer 148, a reaction mixture concentration analyzer 150, the alkylene feed flow meter 124, an alkylene feed flow controller 152, an alkylene feed analyzer controller 154, a gaseous chlorine-containing promoter species flow controller 156, and a net product flow meter 158. The controller 114 is preferably implemented in a computerized control system and also includes a CPU and a memory as well as outputs that are ultimately used to adjust control valves 160 (gaseous chlorine-containing promoter species) and 144 (coolant), respectively. The controller 114 may also determine the yield of alkylene oxide based on the flow rate of alkylene in alkylene feed stream 116, the flow rate of net product in net product stream 132, and the concentration of alkylene oxide in the reactor outlet stream 128.

The controller 114 can also receive concentration data for gaseous chlorine-containing promoter species such as ethyl chloride, vinyl chloride, and ethylene dichloride in reaction mixture 122 from analyzer 150, as well as the concentration of ethylene, ethane, and any other non-chlorinated hydrocarbons in reaction mixture 122. The concentration data is then used to calculate the overall catalyst chloriding effectiveness (e.g., $Z^*$). The controller 114 may also receive a user entered set-point for the mole percent of alkylene oxide in the reactor outlet stream 128 and/or the yield of alkylene oxide. Based on the user entered set point and data from reactor outlet stream concentration analyzer 148, controller 114 can determine if the concentration of alkylene oxide in the reactor outlet stream 128 and/or the yield of alkylene oxide is within the preferred operating condition. When the alkylene oxide concentration and/or yield falls outside of the preferred operating condition, controller 114 can either adjust the reactor temperature or the flow rate of the gaseous chlorine-containing promoter species in the reaction mixture 122 (to change $Z^*$) to obtain the desired alkylene oxide concentration or yield.

As shown in FIG. 8, the alkylene feed analyzer controller 154 can be provided to regulate the alkylene concentration in the reaction mixture 122. In the illustrated example, the alkylene feed analyzer controller 154 receives compositional data from reaction mixture concentration analyzer 150 indicating the amount of alkylene in the reaction mixture 122. The alkylene feed analyzer controller 154 (which may have a user-entered set point for the alkylene concentration in reaction mixture 122) then resets the set point of alkylene feed flow controller 156 which receives flow data from alkylene feed flow meter 124 and manipulates the flow of fresh alkylene feed. The illustrated control scheme is merely exemplary and is not meant to limit the scope of the present invention.

The methods used herein may be embodied in a set of computer readable instructions that are stored on a computer readable medium such as a magnetic disk or computer hard drive for use by controller 114. The controller 114 may be implemented in a number of ways, but the use of a computer control system is preferred.

The set points for the controller 114 described above may be determined in a number of ways. They may be inputs to the controller 114 from an external source, for example from manual analysis of operating data. They may also be calculated by the controller 114, itself. For example, if a computer control system is used, the computer control system may be programmed to analyze received inputs and use the data to calculate a slope of the efficiency of the reaction to productivity of the reaction, and use that slope information to calculate the desired overall catalyst chloriding effectiveness or a temperature to operate at the preferred operating condition. If desired, the controller 114 can even be programmed so as to periodically vary the overall catalyst chloriding effectiveness, and analyze the resulting data as described above. Many other methods of implementing the invention by means of controller will be apparent to one skilled in the art.

The alkylene oxide produced by the present epoxidation process may typically be processed to provide further downstream products, such as, for example, 1,2-diols, 1,2-diol ethers, 1,2-carbonates, and alkanolamines. Since the present invention provides an improved epoxidation method, it is contemplated that the improvements provided will carry forward to provide improvements to these downstream processes and/or products. Improved methods for the production of 1,2-diols, 1,2-carbonates, 1,2-diol ethers and alkanolamines are thus also provided herein.

The conversion of alkylene oxides into 1,2-diols or 1,2-diol ethers may comprise, for example, reacting the desired alkylene oxide with water, suitably in the presence of an acidic or basic catalyst. For example, for preferential production of the 1,2-diol over the 1,2-diol ether, the alkylene oxide may be reacted with a tenfold molar excess of water, in a liquid phase reaction in the presence of an acid catalyst, e.g., 0.5-1.0 wt % sulfuric acid, based on the total reaction mixture, at 50-70° C. at 1 bar absolute, or in a gas phase reaction, at 130-240° C. and 20-40 bar absolute, preferably in the absence of a catalyst. If the proportion of water is lowered, the proportion of the 1,2-diol ethers in the reaction mixture will be increased. The 1-2, diol ethers thus produced may comprise di-ethers, tri-ethers, tetra-ethers or other multi-ethers. Alternative 1,2-diol ethers may be prepared by converting the alkylene oxide with an alcohol, such as methanol or ethanol, or by replacing at least a portion of the water with the alcohol. The resulting 1,2-diols and diol ethers may be utilized in a wide variety of end-use applications in the food, beverage, tobacco, cosmetic, thermoplastic polymer, curable resin system, detergent, heat transfer system, etc., industries.

The conversion of alkylene oxides produced via the method of the present invention into alkanolamines may comprise, for example, reacting the alkylene oxide with ammonia. Anhydrous or aqueous ammonia may be used, although anhydrous ammonia favors the production of monoalkanolamine, and may be used when the same is preferred. The resulting alkanolamines may be used, for example, in the treatment of natural gas. The olefin oxide, may be converted into the corresponding 1,2-carbonate by reacting the olefin oxide with carbon dioxide. If desired, a 1,2-diol may be prepared by subsequently reacting the 1,2-carbonate with water or an alcohol to form the 1,2-diol. For applicable methods, reference is made to U.S. Pat. No. 6,080,897, which is incorporated herein by reference.

Ethylene glycol is used in two significant applications: as a raw material for poly(ethylene terephthalate) for use in polyester fiber, film, and containers, and as an automotive antifreeze. Di-, tri-, and tetraethylene glycols are coproducts of ethylene glycol.

Without further elaboration, it is believed that one skilled in the art can, using the description herein, utilize the present invention to its fullest extent. The following examples are included to provide additional guidance to those skilled in the art in practicing the claimed invention. The examples provided are merely representative of the work that contributes to the teaching of the present application. Accordingly, these examples are not intended to limit the invention, as defined in the appended claims, in any manner.

EXAMPLE 1

This example illustrates the determination of the preferred operating condition using the plot method as described by the flow chart 50 and illustrated by the plot 60.

An alpha-alumina support is prepared using the general procedure as described in Patent Publication WO 2007/123932 and US Publication No. 2007-0111886 A1, incorporated herein by reference. A silver catalyst containing rhenium is prepared on the above alpha-alumina support using the general procedure as described in Patent Publication WO 2007/123932. X-Ray Fluorescence (XRF) analysis of the silver catalyst shows that it contains about 34.8 weight percent silver, about 572 ppmw cesium, about 60 ppmw total sodium, about 405 ppmw rhenium, about 115 ppmw sulphate and about 115 ppmw manganese. Lithium is also added as a promoter during the preparation of the catalyst, however it has not been analyzed using XRF. An 80-cc sample of the silver catalyst is run in a back-mixed autoclave reactor with an inlet gas composition having 30 mole percent ethylene, 3 mole percent carbon dioxide, 8 mole percent oxygen, 0.5 mole percent ethane, concentrations of ethyl chloride in a range of 1.5 to 4 ppmv and the balance being nitrogen. The reactor pressure is 2000 kPa absolute (275 psig). The reactor is started up and operated for one day at a temperature of 230° C. and then run at temperatures of 240° C., 245° C. and 250° C. The total reactor inlet feed gas flow is 10.67 standard liters per minute measured as nitrogen (22.6 scfh).

A first data set on efficiency and productivity at a temperature of 245° C. is obtained by running the reactor at inlet ethyl chloride concentrations of 2.0, 2.5, 3.0 and 3.5 ppmv ($Z^*$ of 2.5, 3.1, 3.7 and 4.4), and the data are provided in Table 1. The productivity is defined by the molar percentage of ethylene oxide in the outlet stream of the reactor and expressed as % EO. A second data set on efficiency and productivity at a temperature of 250° C. is obtained by running the reactor at inlet ethyl chloride concentrations of 2.9, 3.5 and 4.0 ppmv ($Z^*$ of 3.6, 4.4 and 5.0), and the results are provided in Table 1. A first plot of efficiency against productivity is plotted as shown in FIG. 5, to obtain the first curve 34 and the second curve 64, respectively. The symbols represent the actual experimental data and the dotted curve corresponds to the fitted curve. The tangent line 72 is drawn across the first curve 34 and the second curve 64 and the preferred operating conditions at 245 and 250° C. correspond to the points 74 and 76, respectively, on the tangent line 72.

TABLE 1

| Temperature (245° C.) | | | Temperature (250° C.) | | |
|---|---|---|---|---|---|
| $Z^*$ | efficiency | % EO | $Z^*$ | efficiency | % EO |
| 2.5 | 85.5% | 1.72% | 3.6 | 85.3% | 2.09% |
| 3.1 | 85.8% | 1.92% | 4.4 | 85.0% | 2.30% |
| 3.7 | 85.5% | 2.09% | 5.0 | 83.8% | 2.47% |
| 4.4 | 84.5% | 2.26% | | | |

At a temperature of 245° C., preferred operating condition 74 produces 2.00% EO with 85.7% efficiency and the corresponding overall catalyst chloriding effectiveness value is determined by linear regression of the % EO vs. $Z^*$ response data obtained at 245° C. to be 3.43 $Z^*$; at a temperature of 250° C., preferred operating condition 76 produces 2.22% EO with 85.3% efficiency and the corresponding overall catalyst chloriding effectiveness value is similarly determined by linear regression of the % EO vs. $Z^*$ response data obtained at 250° C. to be 4.07 $Z^*$. Table 2, provides a comparison when the reaction is operated at maximum efficiency (36, 66 of FIG. 5) to the preferred operating condition (74, 76 of FIG. 5). As seen from the Table 2, the preferred operating condition provides higher productivity as compared to the reaction run at maximum efficiency. The equivalent productivity of 1.90% EO achieved at the efficiency-maximizing $Z^*$ of 3.1 at 245° C. can be attained for a preferred operating condition according to equations (V) and (VI) at a lower temperature of 242.7° C. and 3.1 $Z^*$, with resulting efficiency on the tangent line of 85.9%.

TABLE 2

| efficiency at 36 | efficiency at 74 | % EO at 36 | % EO at 74 |
|---|---|---|---|
| 85.8% | 85.7% | 1.90% | 2.00% |
| efficiency at 66 | efficiency at 76 | % EO at 66 | % EO at 76 |
| 85.4% | 85.3% | 2.15% | 2.22% |

EXAMPLE 2

This example illustrates performing the epoxidation reaction at the preferred operating condition for a cumulative alkylene oxide production of at least about 250 kmole per m$^3$ of the catalyst.

A silver catalyst containing rhenium is prepared on the alpha-alumina support using the procedure as described in Example 1. The rhenium content of the catalyst is about 368 ppmw as analyzed by X-Ray Fluorescence. A sample of this catalyst is charged to a tubular reactor. The tubular reactor is configured such that a portion of a reactor outlet stream containing carbon dioxide is recycled after passing through an ethylene oxide absorber, and combined with sufficient fresh feed gases to achieve target inlet feed and re-introduced in to the reactor. The reactor is started up and the epoxidation reaction is operated under a range of process conditions for the first 50 days.

The reactor is operated between Day 51 and Day 61 by maintaining an inlet gas composition of 35 mole percent ethylene, 8.5 mole percent oxygen, 0.9 mole percent carbon dioxide, 0.6 mole percent ethane and the balance being gaseous chlorine-containing promoter species as given below, and nitrogen, at a temperature of about 222° C., a reactor pressure of 2140 kPa absolute (295 psig) and a gas hourly space velocity of about 5400 per hour.

On Day 51 and Day 52, corresponding to operation at a first operating condition, an ethyl chloride concentration at the inlet is adjusted such that an overall catalyst chloriding effectiveness value value Z* after accounting for other gaseous chlorine-containing promoter species contained within the stream recycled from the reactor outlet is about 2.7. On Day 52, the average molar percentage of ethylene oxide in the outlet stream of the reactor, i.e., the productivity is 2.15 mole percent and the average efficiency is 86.8%. On Day 53, the inlet ethyl chloride concentration is increased to obtain a Z* value of 3.0 with the productivity of 2.24 mol percent and an average efficiency of 86.5%. A derivative of efficiency (expressed in percent) to productivity (expressed in mole percent) of the epoxidation reaction as a function of overall catalyst chloriding effectiveness value at the constant operating temperature between days 52 and 53 is about −3.3 and is determined to correspond to a preferred operating condition.

From Day 53 till Day 61 the temperature is held at 222° C. with a Z* value of 3.0. Over this period, the cumulative ethylene oxide production is about 1160 kmole per cubic meter of catalyst with the average molar percentage of ethylene oxide in the outlet stream being 2.24 mole % EO and the average efficiency being 86.4%. This run continues for a total of 170 days and the operating temperature on Day 170 is 240° C.

EXAMPLE 3

An 80 cc sample of the used catalyst of Example 2 is obtained from an outlet section of the catalyst bed. The epoxidation reaction is started up with the used catalyst in a back-mixed Berty-type autoclave reactor with an inlet gas composition of 30.0 mol percent ethylene, 8.0 mol percent oxygen, 2.0 mol percent carbon dioxide, 0.5 mol percent ethane, 2.0 ppmv ethyl chloride and the balance being nitrogen. The reactor pressure is 2000 kPa absolute (275 psig) and temperature is 230° C. The total reactor inlet feed gas flow is 640 standard liters per hour measured as nitrogen. After four days of operation at 230° C., the temperature is increased to 240° C.

Figure 9:
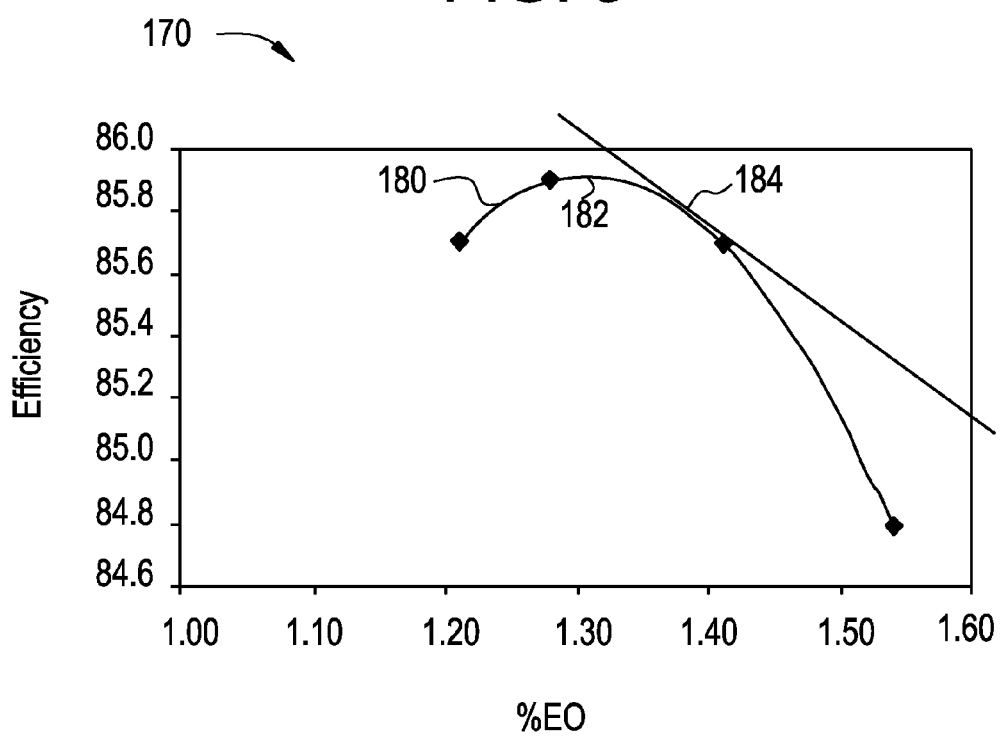
FIG. 9 is another plot of efficiency against productivity of an epoxidation reaction, according to embodiments of the present invention.

A first data set on efficiency and productivity at a temperature of 240° C. is obtained by varying the inlet ethyl chloride concentration in steps of 0.3 ppmv to obtain Z* value in the range of about 3.1 to 4.3, and is provided in Table 3. A first plot 170 of efficiency against productivity is plotted and is given in FIG. 9.

TABLE 3

| Z* | % EO | efficiency |
|---|---|---|
| 3.16 | 1.21 | 85.7 |
| 3.48 | 1.28 | 85.9 |
| 3.91 | 1.41 | 85.7 |
| 4.34 | 1.54 | 84.8 |

The first data set is mathematically fitted as a parabola to obtain a first curve 180 which predicts a maximum efficiency of 85.9% (point 182) with a corresponding productivity of 1.31 mole percent EO at a temperature of 240° C. The corresponding Z* value is 3.58 at point 182. A preferred operating condition at 240° C. corresponds to point 184, where a derivative of efficiency to productivity or slope of the first curve is about −3.0. At point 184, the efficiency is 85.8% and the productivity is 1.38 mole percent EO and the corresponding Z* value is 3.81. This Example illustrates that operating the reactor at preferred operating conditions as opposed to operating at maximum efficiency results in higher productivity for a given temperature.

While only certain features of the invention have been illustrated and described herein, many modifications and changes will occur to those skilled in the art. It is, therefore, to be understood that the appended claims are intended to cover all such modifications and changes as fall within the true spirit of the invention.

What is claimed is:

1. A method of producing ethylene oxide comprising:
passing a reaction mixture comprising ethylene, oxygen and a gaseous chlorine-containing promoter species over a supported catalyst comprising silver and a promoting amount of rhenium to undergo an epoxidation reaction at a first operating condition to form ethylene oxide in a reactor; and subsequently performing the epoxidation reaction within the reactor at a preferred operating condition, wherein the preferred operating condition is characterized by an efficiency of the epoxidation reaction toward the ethylene oxide, wherein the efficiency is lower than that of a maximum efficiency achievable at an operating temperature corresponding to the preferred operating condition, wherein the preferred operating condition is further characterized by a productivity of the epoxidation reaction, wherein the productivity of the epoxidation reaction at the preferred operating condition is higher than that obtained at the maximum efficiency achievable at the operating temperature corresponding to the preferred operating condition and wherein the preferred operating condition is further characterized by an overall catalyst chloriding effectiveness value that is higher than when the epoxidation reaction is performed at the maximum efficiency achievable at the operating temperature corresponding to the preferred operating condition and wherein the reactor is operated at the preferred operating condition for a cumulative ethylene oxide production of at least 250 kmole per $m^3$ of the catalyst.

2. The method of claim 1, wherein subsequently performing the epoxidation reaction at the preferred operating condition comprises varying at least one of a temperature of the first operating condition, or an overall catalyst chloriding effectiveness value of the first operating condition.

3. The method of claim 1 further comprising determining the preferred operating condition.

4. The method of claim 1, wherein the gaseous chlorine-containing promoter species is selected from a group consisting of C1-C8 chlorohydrocarbons and any mixtures thereof.

5. The method of claim 1, wherein the catalyst comprises rhenium in a range of about 180 ppmw to about 2000 ppmw.

6. The method of claim 5, wherein the catalyst further comprises at least one co-promoter, wherein the co-promoter comprises halides and/or oxyanions of elements other than oxygen having an atomic number of 5 to 83 and being from the groups 3b to 7b, and 3a to 7a, of the Periodic Table.

7. The method of claim 6, wherein the catalyst further comprises at least one co-promoter selected from a group consisting of Group IA metals, Group IIA metals, phosphorus, boron, manganese, sulfur, molybdenum, tungsten, chromium, titanium, hafnium, zirconium, vanadium, thallium, thorium, tantalum, niobium, gallium, germanium and any mixtures thereof.

8. A method of using ethylene oxide for preparing a 1,2-diol, a 1,2-diol ether, a 1,2-carbonate or an alkanolamine comprising converting the ethylene oxide into the 1,2-diol, 1,2-diol ether, 1,2-carbonate or alkanolamine, wherein the ethylene oxide has been obtained by a process for the production of ethylene oxide according to claim 1.

9. The method of claim 1, where the reactor is operated at the preferred operating condition for a cumulative ethylene oxide production of at least 500 kmole per m$^3$ of the catalyst.

10. The method of claim 9, wherein the reactor is operated at the preferred operating condition for a cumulative ethylene oxide production of at least 1000 kmole per m$^3$ of the catalyst.

* * * * *